(12) United States Patent
Seiler et al.

(10) Patent No.: US 8,911,427 B2
(45) Date of Patent: Dec. 16, 2014

(54) THERAPEUTIC AGENT RESERVOIR DELIVERY SYSTEM

(75) Inventors: Peter M. Seiler, St. Anthony Village, MN (US); Kenneth E. Cobian, St. Anthony, MN (US); Genevieve L. Gallagher, Mendota Heights, MN (US); Zhongping C. Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 699 days.

(21) Appl. No.: 12/979,580

(22) Filed: Dec. 28, 2010

(65) Prior Publication Data

US 2012/0165795 A1    Jun. 28, 2012

(51) Int. Cl.
*A61K 9/22*    (2006.01)
*A61K 9/00*    (2006.01)
*A61K 31/496*    (2006.01)
*A61K 31/65*    (2006.01)
*A61K 9/70*    (2006.01)

(52) U.S. Cl.
CPC .............. *A61K 9/0024* (2013.01); *A61K 31/496* (2013.01); *A61K 31/65* (2013.01); *A61K 9/7084* (2013.01)
USPC ....................................... 604/891.1

(58) Field of Classification Search
USPC ............. 424/423, 424, 426; 604/890.1, 891.1
See application file for complete search history.

(56) References Cited

U.S. PATENT DOCUMENTS

| | | |
|---|---|---|
| 4,226,848 A | 10/1980 | Nagai et al. |
| 4,917,686 A | 4/1990 | Bayston et al. |
| 4,968,539 A | 11/1990 | Aoyagi et al. |
| 5,217,493 A | 6/1993 | Raad et al. |
| H1465 H | 7/1995 | Stokes |
| 5,447,724 A | 9/1995 | Helmus et al. |
| 5,624,704 A | 4/1997 | Darouiche et al. |
| 5,722,992 A | 3/1998 | Goldmann |
| 5,756,145 A | 5/1998 | Darouiche |
| 5,766,248 A | 6/1998 | Donovan |
| 5,856,367 A | 1/1999 | Barrows et al. |
| 5,897,590 A | 4/1999 | Donovan |
| 5,902,283 A | 5/1999 | Darouiche et al. |
| 6,099,562 A | 8/2000 | Ding et al. |
| 6,162,487 A | 12/2000 | Darouiche |
| 6,275,728 B1 | 8/2001 | Venkatraman et al. |
| 6,284,305 B1 | 9/2001 | Ding et al. |

(Continued)

FOREIGN PATENT DOCUMENTS

| | | |
|---|---|---|
| CN | 1984686 A | 6/2007 |
| EP | 0640661 A2 | 3/1995 |

(Continued)

OTHER PUBLICATIONS

Office Action for U.S. Appl. No. 12/725,072, mailed Feb. 2, 2012, 7 pages.

(Continued)

*Primary Examiner* — Bhisma Mehta
*Assistant Examiner* — Bradley Osinski

(57) ABSTRACT

A therapeutic agent reservoir comprises a reservoir body comprising a polymer and a therapeutic agent mixed within the polymer, and an outer coating enclosing the reservoir body, wherein at least a portion of the outer coating comprises a rate-controlling membrane configured to provide a predetermined release rate of the therapeutic agent through the rate-controlling membrane.

12 Claims, 8 Drawing Sheets

(56) References Cited

U.S. PATENT DOCUMENTS

| | | | |
|---|---|---|---|
| 6,319,512 | B1 | 11/2001 | Rothen-Weinhold et al. |
| 6,475,434 | B1 | 11/2002 | Darouiche et al. |
| 6,562,363 | B1 * | 5/2003 | Mantelle et al. ............ 424/434 |
| 6,599,275 | B1 | 7/2003 | Fischer, Jr. |
| 6,635,078 | B1 | 10/2003 | Zhong et al. |
| 6,663,662 | B2 | 12/2003 | Pacetti et al. |
| 6,855,777 | B2 | 2/2005 | McLoughlin et al. |
| 6,887,270 | B2 | 5/2005 | Miller et al. |
| 6,933,026 | B2 | 8/2005 | Mauze et al. |
| 6,949,254 | B2 | 9/2005 | Gen |
| 6,968,234 | B2 | 11/2005 | Stokes |
| 7,063,682 | B1 | 6/2006 | Whayne et al. |
| 7,245,973 | B2 | 7/2007 | Liu et al. |
| 7,390,523 | B2 | 6/2008 | Pacetti et al. |
| 7,410,497 | B2 | 8/2008 | Hastings et al. |
| 7,419,709 | B2 | 9/2008 | Rypacek et al. |
| 7,534,241 | B2 | 5/2009 | Coppeta et al. |
| 7,596,408 | B2 | 9/2009 | Singhal et al. |
| 7,621,906 | B2 | 11/2009 | Pastore et al. |
| 7,622,146 | B2 | 11/2009 | Roorda et al. |
| 2003/0086963 | A1 | 5/2003 | Scamilla Aledo et al. |
| 2003/0143256 | A1 | 7/2003 | Gen |
| 2003/0161870 | A1 | 8/2003 | Hsu et al. |
| 2003/0203015 | A1 | 10/2003 | Aledo et al. |
| 2003/0204239 | A1 | 10/2003 | Carlyle et al. |
| 2004/0048016 | A1 | 3/2004 | Wang et al. |
| 2004/0186528 | A1 | 9/2004 | Ries et al. |
| 2005/0037052 | A1 | 2/2005 | Udipi et al. |
| 2005/0079199 | A1 | 4/2005 | Heruth et al. |
| 2005/0244453 | A1 | 11/2005 | Stucke et al. |
| 2005/0267543 | A1 | 12/2005 | Heruth et al. |
| 2005/0271701 | A1 | 12/2005 | Cottone, Jr. et al. |
| 2006/0009806 | A1 | 1/2006 | Heruth et al. |
| 2006/0039946 | A1 | 2/2006 | Heruth et al. |
| 2006/0051392 | A1 | 3/2006 | Heruth et al. |
| 2006/0051393 | A1 | 3/2006 | Heruth et al. |
| 2006/0095020 | A1 | 5/2006 | Casas et al. |
| 2006/0216403 | A1 | 9/2006 | Hayes |
| 2006/0240065 | A1 | 10/2006 | Chen |
| 2007/0010632 | A1 | 1/2007 | Kaplan et al. |
| 2007/0198063 | A1 | 8/2007 | Hunter et al. |
| 2007/0212381 | A1 | 9/2007 | DiFiore et al. |
| 2008/0014236 | A1 | 1/2008 | Pacetti et al. |
| 2008/0014245 | A1 | 1/2008 | Pacetti et al. |
| 2008/0075628 | A1 | 3/2008 | Judd et al. |
| 2008/0125728 | A1 | 5/2008 | Bischoff et al. |
| 2008/0128315 | A1 | 6/2008 | Buevich et al. |
| 2008/0132922 | A1 | 6/2008 | Buevich et al. |
| 2008/0208325 | A1 | 8/2008 | Helmus et al. |
| 2008/0241212 | A1 | 10/2008 | Moses et al. |
| 2008/0241245 | A1 | 10/2008 | Myers et al. |
| 2008/0243241 | A1 | 10/2008 | Zhao |
| 2008/0260796 | A1 | 10/2008 | Bischoff et al. |
| 2009/0041824 | A1 | 2/2009 | Zugates et al. |
| 2009/0081272 | A1 | 3/2009 | Clarke et al. |
| 2009/0198063 | A1 | 8/2009 | Kiyoto et al. |
| 2009/0198197 | A1 | 8/2009 | Bischoff et al. |
| 2009/0280153 | A1 | 11/2009 | Hunter et al. |
| 2009/0292327 | A1 | 11/2009 | Singhal et al. |
| 2010/0158970 | A1 | 6/2010 | Tipton et al. |
| 2010/0198278 | A1 | 8/2010 | Cobian et al. |
| 2010/0203100 | A1 | 8/2010 | Cobian et al. |
| 2010/0278894 | A1 | 11/2010 | Burgmeier |
| 2010/0278895 | A1 | 11/2010 | Burgmeier |

FOREIGN PATENT DOCUMENTS

| | | | |
|---|---|---|---|
| EP | 2016939 | A1 | 1/2009 |
| WO | WO 95/05138 | A1 | 2/1995 |
| WO | WO 96/39215 | A1 | 12/1996 |
| WO | WO 98/15317 | A1 | 4/1998 |
| WO | WO 01/64258 | A1 | 9/2001 |
| WO | WO 01/66159 | A1 | 9/2001 |
| WO | WO 01/66162 | A1 | 9/2001 |
| WO | 0205788 | A1 | 1/2002 |
| WO | 0213783 | A2 | 2/2002 |
| WO | 03000156 | A1 | 1/2003 |
| WO | 03028660 | A2 | 4/2003 |
| WO | WO 2004/026361 | A1 | 4/2004 |
| WO | WO 2004/084955 | A1 | 10/2004 |
| WO | 2005000268 | A2 | 1/2005 |
| WO | 2005007035 | A1 | 1/2005 |
| WO | 2005051234 | A2 | 6/2005 |
| WO | WO 2005/058414 | A1 | 6/2005 |
| WO | 2005061003 | A1 | 7/2005 |
| WO | 2005072703 | A2 | 8/2005 |
| WO | 2006039330 | A1 | 4/2006 |
| WO | 2008024149 | A2 | 2/2008 |
| WO | 2008027783 | A2 | 3/2008 |
| WO | WO 2008/039917 | A2 | 4/2008 |
| WO | WO 2008/039923 | A2 | 4/2008 |
| WO | WO 2008/117268 | A2 | 10/2008 |
| WO | WO 2008/131089 | A2 | 10/2008 |
| WO | 2010088682 | A2 | 8/2010 |
| WO | 2010088697 | A2 | 8/2010 |

OTHER PUBLICATIONS

Kuhn et al., "Antimicrobial Implant Coating in Arthroplasty," Local Antibiotics in Arthroplasty (ISBN 9783131346414). 2007, pp. 23-29.

Vogt et al., "Resorbable Antibiotic Coatings for Bone Substitutes and Implantable Devices," Mat-wiss u. Werkstofftech, 2005, 36, No. 12, pp. 814-819.

Vogt et al., "Design of an Antibiotic Delivery System Based on a Bioresorbable Bone Substitute," Advanced Engineering Materials 2007, 9, No. 12, pp. 1135-1140.

Stemberger et al., "New Antibiotic Carriers and Coatings in Surgery," Local Antibiotics in Arthroplasty (ISBN 9783131346414), 2007, pp. 13-21.

Mizrahi et al., "Adhesive Tablet Effective for Treating Canker Sores in Humans," Journal of Pharmaceutical Sciences, vol. 93, No. 12, Dec. 2004, pp. 2927-2935.

Matl, "New Anti-Infective Coatings of Medical Implants," Antimicrobial Agents and Chemotherapy, vol. 52, No. 6, Jun. 2008, pp. 1957-1963.

Letsch et al., "Local antibiotic administration in osteomyelitis treatment—a comparative study with two different carrier substances," Aktuelle Traumatol, Nov. 1993, 23(7): 324-9 (translation of abstract included).

Von Hasselbach et al., "Clinical aspects and pharmacokinetics of collagen-gentamicin as adjuvant therapy of osseous infections," Unfallchirurg, Sep. 1989, 92(9):459-70 (translation of abstract included).

Hettfleisch et al., "Release of gentamicin from biomaterials implanted into the lumen of intermedullary local carriers—a pharmacokinetic study," Aktuelle Traumatol, Apr. 1993, 23(2): 68-71 (translation of abstract included).

Attmanspacher et al., "Medium-term results in the treatrnent of post-operative septic arthritis of the shoulder," Unfallchirurg Springer-Verlag, 2000, 103:1048-1056.

"CollaRx® Gentamicin Surgical Implant: Ex-US," http://www.innocollinc.com/index.php/CollaRx-Gentamicin-Surgical-Implant--Ex-US.html, accessed on Jun. 16, 2009, 3 pp.

Ipsen et al., "Gentamicin-collagen sponge for local applications," Acta Orthop Scand, Dec. 1991, 62(6):592-4.

Jerosch et al., "Septic Arthritis: Arthroscopic Management With Local Antibiotic Treatment," Acta Orthopaedica Belgica, 1995, 61 (2): 126-34.

Jerosch et al., "Arthroscopic treatment of Septic Arthritis—Surgical Technique," Unfallchirurg, Jun. 1998, 101(6):454-60 (translation of abstract included).

Eklund, "Prevention of sternal wound infections with locally administered gentamicin," APMIS 115:1022-1024, 2007.

Gomez et al., "Effectiveness of collagen-gentamicin implant for treatment of 'dirty' abdominal wounds," World J Surg, 1999; 23: 123-127 (translation of abstract included).

(56) References Cited

OTHER PUBLICATIONS

Musella et al., "Collagen tampons as aminoglycoside carriers to reduce postoperative infection rate in prosthetic repair of groin hernias," Eur J Surg, 2001; Feb.;167(2):130-2.
Nowacki et al., "Prospective, randomized trial examining the role of gentamycin-containing collagen sponge in the reduction of postoperative morbidity in rectal cancer patients: early results and surprising outcome at 3-year follow-up," Int J Colorectal DIS, 2005; 20:114-120.
Rutten et al., "Prevention of wound infection in elective colorectal surgery by local application of gentamicin-containing sponge,"Eur J Surg Suppl, 1997; (578):31-5.
Vogel et al., "Treatment of pilonidal sinus with excision and primary suture using a local, resorbable antibiotic carrier. Results of a randomized prospective study," Chirurg, 1992; Sep.;63(9):748-53 (translation of abstract included).
Stemberger et al., "Local treatment of bone and soft tissue infections with collagen-gentamicin sponge," Eur J Surg Suppl, 1997; 578:17-26.
Nielsen et al., "Contaminated fistula following J-pouch ileoanal reservoir (Case Report)," Eur J Surg, Mar. 1991; 157(3):219-20.
Kallehave et al., "Topical antibiotics used in the treatment of complex wounds: A discussion of the use of collagen sponges impregnated with gentamicin in the treatment of six patients with complicated, infected, soft tissue wounds following gastrointestinal surgery," Journal of Wound Care. 1996; vol. 5, No. 4, pp. 155-160.
Lampe et al., "Necrosectomy with an Ultrasonic Dissector in the Treatment of Necrotizing Pancreatitis," Acta Chir Bleg, 2006; vol. 106, 177-180.
Meyer et al., "Perineal wound closure after abdominal-perineal excision of the rectum," Tech Coloproctol, 2004; 8:s230-s234.
Leyh et al., "Adjuvant treatment of deep sternal wound infections with collagenous gentamicin," Ann Thorac Surg, 1999; Nov. 68(5): 1648-51.
Eklund el al., "Prophylaxis of sternal wound infections with gentamicin-collagen implant: randomized controlled study in cardiac surgery," Journal of Hospital Infection, 2005; 59:108-112 (translation of abstract included).
Friberg et al., "Antibiotic concentrations in serum and wound fluid after local gentamicin or intravenous dicloxacillin prophylaxis in cardiac surgery," Scand J Infect Dis, 2003; 35(4):251-4.
Friberg el al., "Local gentamicin reduces the sternal wound infections after cardiac surgery: a randomized controlled trial," Ann Thorac Surg, 2005; Jan.; 79(1): 153-61.
Friberg et al., "Cost effectiveness of local collagen gentamicin as prophylaxis for sternal wound infections in different risk groups," Scandinavian Cardiovascular Journal, 40, 2006, pp. 117-125.
Friberg et al., "Influence of more than six sternal fixation wires on the incidence of deep sternal would infection," Thioac Cardiov Surg, 2006; 54:468-473.
Friberg et al., "Incidence, microbiological findings , and clinical presentation of sternal wound infections after cardiac surgery with and without gentamicin prophylaxis," Eur J Clin Microbiol Infect Dis, 2007; 26: 91-97.
Horch et al., "Prevention of infection in Teflon prostheses for dialysis access: experiences with a resorbable combined collagen-antibiotic system," Vasa, 1989; 18(1):30-4 (translation of abstract included).

Jorgensen et al., "Clinical and pharmacokinetic evaluation of gentamicin-containing collagen in groin wound infections after vascular reconstruction," Eur J Vasc Surg, Feb. 1991; 5(1):87-91.
Belz et al., "Use of gentamicin-collagen fleece in vascular surgery," Angio, 1989: 11(14): 147-152 (translation of abstract included).
Holdsworth, "Treatment of infective and potentially infective complications of vascular bypass grafting using gentamicin with collagen sponge, "Ann R Coll Surg Engl, May 1999; 81(3): 166-70.
Rohde, "Spondylodiscitis after Lumbar Discectomy: Incidence and a Proposal for Prophylaxis," Spine, 1998; vol. 23, No. 5, pp. 615-620.
Kolodziejcyk, "Epidural 'Sulmycin Implant'—coverage of local infection prophylaxis in surgical treatment of penetrating head injuries," Akt Traumatol, 1992; 22: 272-275 (translation of abstract included).
Zink et al., "Prophylaxis of postoperative lumbar spondylodiscitis," Neurosurg Rev, 1989; 12(4): 297-303.
Arlt el al., "Diabetic Foot," Langenbecks Arch Chir, 1997; Suppl II, pp. 528-532 (translation of abstract included).
Faludi et al., "Experience Acquired by Applying Gentamicin-Sponge," Acta Chirurgica Hungarcia, 1997; 36(14): 81-82.
Kwasny et al., "The use of gentamicin collagen floss in the treatment of infections in trauma surgery," Orthopedics, May 1994, 17(5):421-425.
Castor, "Local Antibiotic Therapy via a Fistula: Treatment of a Postoperative Abscess with Collagen and Gentamicin," Scand J Infect, 1999; 31:216.
Schafer et al., "Is the Primary Suture Indicated in Infected Wounds in Pediatric Surgery," Langenbecks Arch Chir Supp II, Kongrebeacht, 1997; 1, pp. 1350-1352 (translation of abstract included).
Friberg, "Local collagen-gentamicin for prevention of sternal wound infections: the LOGIP trial," APMIS 115: 1016-21, 2007.
Friberg et al, "Collagen-gentamicin for prevention of sternal wound infection; long-term follow-up of effectiveness," Interactive CardioVascular and Thoracic Surgery, 9(2009):454-458.
Peerdeman et al., "In situ treatment of an infected intrathecal baclofen pump implant with gentamicin-impregnated collagen fleece," Technical note, J Neurosurg, Sep. 4, 2009, pp. 1-3.
Rusczak et al., "Collagen as a carrier for on-site delivery of antibacterial drugs," Advanced Drug Delivery Reviews 55, 2003, 1679-1698.
Dernevik, "Infection Rates After Pacemaker Operations and Prophylaxis with Gentamicin-Collagen Patches in the Generation Pocket," Europace, vol. 4, (Supplemental 2), Dec. 2003, 2 pp.
Wachol-Drewek, "Comparative Investigation of Drug Delivery Collagen Implants Saturated in Antibiotic Solutions and a Sponge Containing Gentamicin," Biomaterials, vol. 17, No. 17, Oct. 20, 1995, 1733-1738, 6 pp.
Petrie et al., "Pressure Sensitive Adhesives for Health Care," dated Jun. 4, 2004, 2 pp.
TyRx Pharma, Inc. Announces Food and Drug Administration (FDA) 510(k) Clearance of the AIGIS (Rx) (TM) Cardiac Rhythm Medical Device (CRMD) Anti-Bacterial Envelope, an Innovative Mesh Envelope Designed to Immobilize and Reduce Bacterial Infection of a Pacemaker or Implantable Cardioverter Defibrillator (ICD) When Implanted in the Body, Market Wire, Jan. 2008, 2 pp.
International Search Report and Written Opinion of international application No. PCT/US2011/034609, dated Aug. 28, 2012, 25 pp.
International Preliminary Report on Patentability and Written Opinion of international application No. PCT/US2011/034609, dated Jul. 11, 2013, 16 pp.

* cited by examiner

THERAPEUTIC AGENT RESERVOIR DELIVERY SYSTEM

TECHNICAL FIELD

The disclosure relates to implantable medical device and, more particularly, to methods of reducing risk of post-implantation infection.

BACKGROUND

Implantable medical devices (IMDs) include a variety of devices that provide therapy (such as electrical simulation or drug delivery) to a patient, monitor a physiological parameter of a patient, or both. IMDs typically include a number of functional components encased in a housing. The housing is implanted in a body of the patient. For example, the housing may be implanted in a pocket created in a torso of a patient. The housing may be constructed of a biocompatible material, such as titanium. While the housing is biocompatible, there may still be a risk of infection to the patient as a result of the implantation procedure or the presence of the IMD in the body.

SUMMARY

In general, the disclosure is directed to a therapeutic agent reservoir delivery system, such as a system for use as an accessory for an implantable medical device (IMD) to prevent or ameliorate post-implantation infections. The reservoir may be configured to be adhered to or implanted adjacent to the IMD to reduce or substantially eliminate risk of post-implant infection to a patient in which the IMD is implanted.

In one aspect, the present disclosure is directed to a therapeutic agent reservoir comprising a reservoir body comprising a polymer and a therapeutic agent mixed within the polymer, and an outer coating enclosing the reservoir body, wherein at least a portion of the outer coating comprises a rate-controlling membrane configured to provide a predetermined release rate of the therapeutic agent through the rate-controlling membrane.

In another aspect, the present disclosure is directed to a system comprising a therapeutic agent reservoir comprising a reservoir body comprising a polymer and a therapeutic agent mixed within the polymer and an outer coating enclosing the reservoir body, wherein at least a portion of the outer coating comprises a rate-controlling membrane configured to provide a predetermined release rate of the therapeutic agent through the rate-controlling membrane, and an implantable medical device comprising a housing, wherein the therapeutic agent reservoir is adhered to the housing of the implantable medical device.

In yet another aspect, the present disclosure is directed to a method comprising forming a mixture comprising a polymer and a therapeutic agent, forming the mixture into a body, and enclosing the body in an outer coating, wherein at least a portion of the outer coating comprises a rate-controlling membrane configured to provide a predetermined release rate of the therapeutic agent through the rate-controlling membrane.

The details of one or more examples of the disclosure are set forth in the accompanying drawings and the description below. Other features, objects, and advantages of the disclosure will be apparent from the description and drawings, and from the claims.

DETAILED DESCRIPTION

In general, the disclosure is directed to a reservoir for the storage and delivery of a therapeutic agent, wherein the reservoir may be used as an accessory with an implantable medical device (IMD). For example, the reservoir may store an antimicrobial therapeutic agent and may be configured to be adhered to or implanted adjacent to the IMD to reduce or substantially eliminate risk of infection proximate to an implant site at which the IMD is implanted in a body of a patient. A rate-controlling membrane controls the release rate of the therapeutic agent from the reservoir to the patient.

Figure 1:
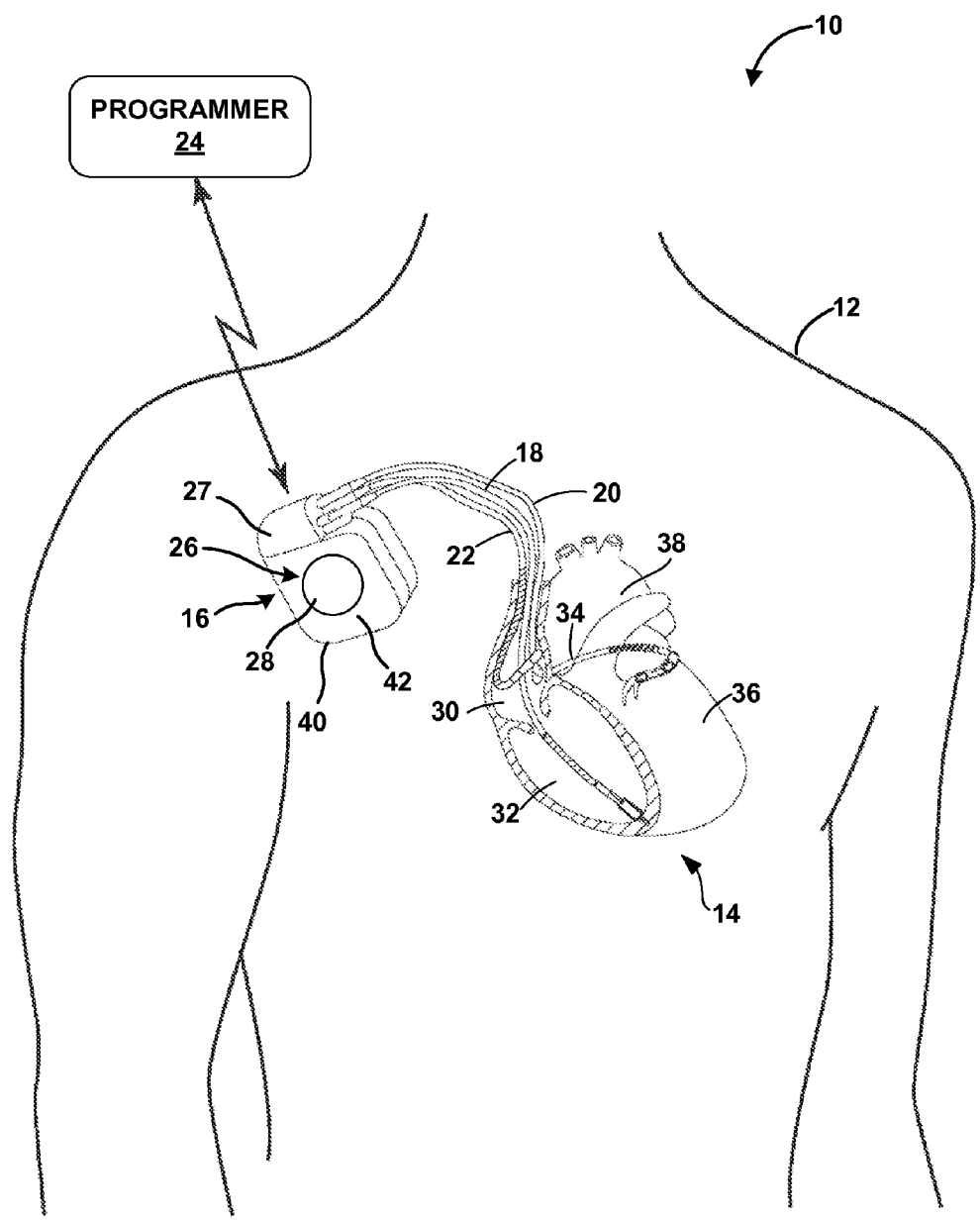
FIG. 1 is a conceptual diagram illustrating an example therapy system that may be used to provide cardiac stimulation therapy to a patient.

FIG. 1 is a conceptual diagram illustrating an example therapy system 10 that may be used to provide therapy to a patient 12. Patient 12 ordinarily, but not necessarily, will be a human. Therapy system 10 may include an implantable medical device (IMD) such as an implantable cardiac device (ICD) 16, and a programmer 24. Therapy system 10 further comprises a therapeutic agent reservoir 26 that may be adhered to a housing 40 of ICD 16 or may be placed proximate to ICD 16, such as in the pocket within patient 12 in which ICD 16 has been implanted. In the example illustrated in FIG. 1, reservoir 26 is adhered to an outer surface 42 of a housing 40. In the example illustrated in FIG. 1, reservoir 26 is in the form of a disk 28, such as a generally circular disk.

While the examples in the disclosure are primarily directed to a reservoir 26 adhered to an ICD 16, in other examples, reservoir 26 may be utilized with other IMDs. For example, reservoir 26 may be attached to an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), a cardiac or neurological lead, a catheter, an orthopedic device such as a spinal device, or the like. In general, reservoir 26 may be attached to or implanted proximate to any medical device configured to be implanted in a body of a patient 12.

In the example depicted in FIG. 1, ICD 16 is connected (or "coupled") to leads 18, 20, and 22 via a connector block 27. ICD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, ICD 16 may deliver pacing pulses, but not cardioversion or defibrillation shocks, while in other examples, ICD 16 may deliver cardioversion or defibrillation shocks, but not pacing pulses. In addition, in further examples, ICD 16 may deliver pacing pulses, cardioversion shocks, and defibrillation shocks.

Leads 18, 20, 22 that are coupled to ICD 16 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, ICD 16 may deliver stimulation therapy to heart 14 by delivering stimulation to an extravascular tissue site in addition to or instead of delivering stimulation via electrodes of intravascular leads 18, 20, 22.

ICD 16 may sense electrical signals attendant to the depolarization and repolarization of heart 14 (e.g., cardiac signals) via electrodes (not shown in FIG. 1) coupled to at least one of the leads 18, 20, 22. In some examples, ICD 16 provides pacing pulses to heart 14 based on the cardiac signals sensed within heart 14. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 32 and 36, and deliver defibrillation therapy to heart 14 in the form of electrical shocks. In some examples, ICD 16 may be programmed to deliver a progression of therapies, e.g., shocks with increasing energy levels, until a fibrillation of heart 14 is stopped. ICD 16 may detect fibrillation by employing one or more fibrillation detection techniques known in the art. For example, ICD 16 may identify cardiac parameters of the cardiac signal, e.g., R-waves, and detect fibrillation based on the identified cardiac parameters.

In some examples, programmer 24 may be a handheld computing device or a computer workstation. Programmer 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with ICD 16. For example, the user may interact with programmer 24 to retrieve physiological or diagnostic information from ICD 16. A user may also interact with programmer 24 to program ICD 16, e.g., select values for operational parameters of ICD 16.

Programmer 24 may communicate with ICD 16 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the ICD 16 implant site in order to improve the quality or security of communication between ICD 16 and programmer 24.

Figure 2:
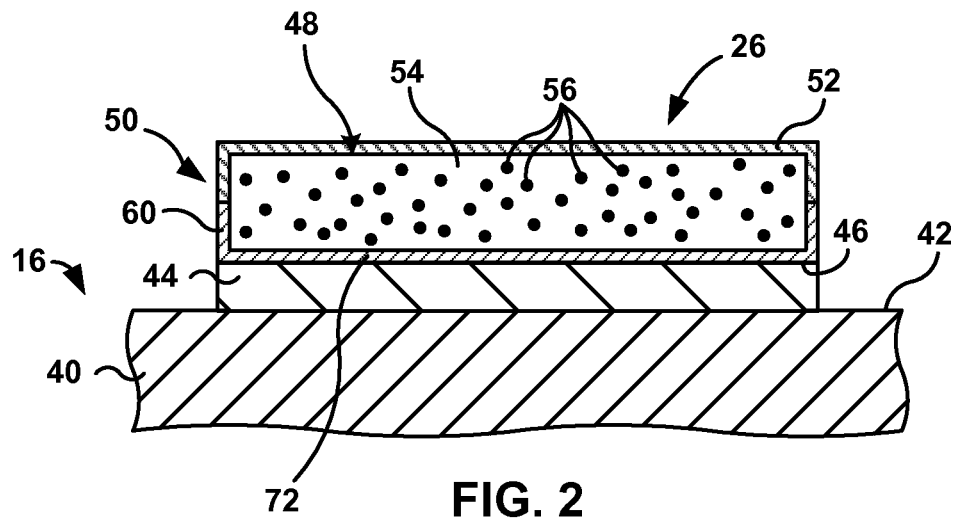
FIG. 2 is a cross-sectional diagram illustrating an example of a reservoir for the delivery of a therapeutic agent, wherein the reservoir may be adhered to a housing of an implantable medical device.

Turning to FIG. 2, in one example, reservoir 26 comprises a reservoir body 48 enclosed within an outer coating 50 wherein at least a portion of outer coating 50 comprises a rate-controlling membrane 52. Reservoir 26 may reduce or substantially eliminate risk of post-implant infection proximate to the implant site of ICD 16 by releasing the therapeutic agent over a period of time subsequent to implantation of ICD 16 in the body of patient 12. In some examples, reservoir 26 may be adhered to an outer surface 42 of housing 40 and/or to connector block 27 of ICD 16 (FIG. 1).

Figure 3:
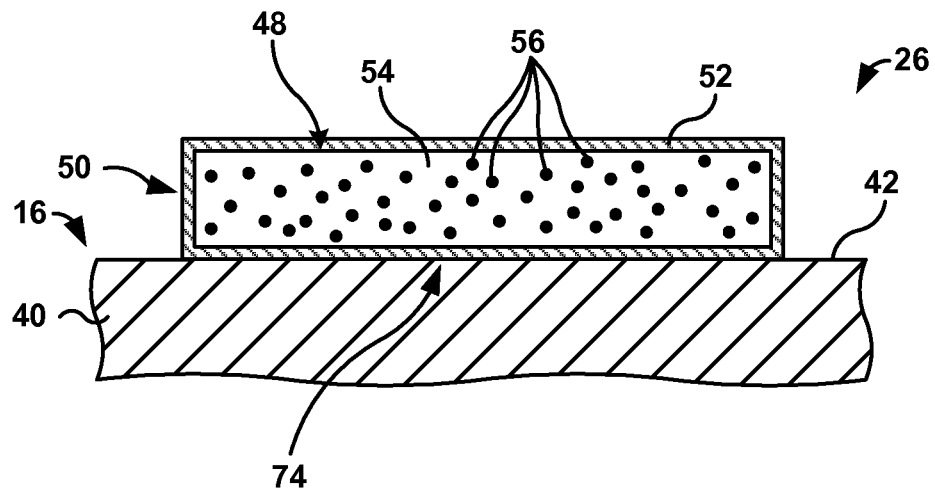
FIG. 3 is a cross-sectional diagram illustrating another example of a reservoir for the delivery of a therapeutic agent, wherein a portion of the reservoir comprises a pressure sensitive adhesive attached to the housing of an implantable medical device.

Reservoir body 48 may comprise a polymer 54 and at least one therapeutic agent 56 (shown conceptually in FIGS. 2 and 3). In one example, therapeutic agent 56 may be mixed into polymer 54 or therapeutic agent 56 may be formed as part of a matrix with polymer 54. In some examples, polymer 54 is a biocompatible polymer. In some examples, biocompatible polymer 54 may be biodegradable or bioabsorbable and be absorbed by the body of patient 12 after implantation of reservoir 26. In other examples, polymer 54 of reservoir body 48 is not biodegradable and may remain in the body of patient 12 after implantation.

In one example, polymer 54 of reservoir body 48 comprises a biocompatible and hydrophilic material that provides for relatively high loading of therapeutic agent 56 in reservoir body 48, relatively high stability of therapeutic agent 56, and relatively fast release of therapeutic agent 56 from reservoir body 48. In some examples, polymer 54 provides a suitable dispersion medium for therapeutic agent 56 so that therapeutic agent 56 may be maintained in a substantially homogenous dispersion for a predetermined period of time via blend uniformity and stability. In some examples, polymer 54 may be bioabsorbable and/or biodegradable within the tissue and/or fluids of patient 12, such that, in some examples, polymer 54, and hence therapeutic agent 56, is completely released within a predetermined time frame, such as within about six months. Because rate-controlling membrane 52 is configured to provide for a selected release rate of the therapeutic agent 56 out of reservoir 26 and into patient 12, as described in more detail below, the material of reservoir body 48, such as polymer 54, may be configured to maximize other properties, such as loading capacity of therapeutic agent 56 in reservoir body 48 (e.g., the mass of therapeutic agent 56 that may be loaded in reservoir body 48 per mass or volume of reservoir body 48) and stability of therapeutic agent 56 in reservoir body 48 (e.g., keeping a substantial portion of therapeutic agent 56 biologically active so that therapeutic agent 56 does not deteriorate before implanting in patient 12), without being concerned about therapeutic agent 56 being released too quickly into patient 12.

Examples of biocompatible hydrophilic materials that may be used for polymer 54 of reservoir body 48 include, but are not limited to, polyvinylpyrrolidone (PVP), glycerol, polyethylene glycol (PEG), methyl polyethylene glycol, polyacrylic acid (PAA), polymethacrylic acid, polylactic acid (PLA), lactic acid, poly(lactic-co-glycolic acid) (PLGA), polycaprolactam, poly(trimethylene carbonate) (PMTC), chitosan, sucrose acetate isobutyrate (SAIB), polyhydroxylalkanoate (PHA), polyhydroxybutyrate (PHB), carboxymethylchitosan-oxidized starch, poloxamers, polymethyl vinyl ether/maleic anhydride, and pluonics such as a polyethylene glycol-polypropylene glycol-polyethylene glycol (PEG-PPG-PEG) pluonic and/or a polypropylene glycol-polyethylene glycol-polypropylene glycol (PPG-PEG-PPG) pluonic. In some examples, N-methylpyrrolidone (NMP) and/or dimethyl sulfoxide (DMSO) may be able to be used to help make biodegradable polymers, such as PLGA into gels. In some examples, reservoir body 48 comprises between about 40 weight % and about 90 weight % of reservoir body 48, such as between about 50 weight % and about 70 weight % of reservoir body 48. In one example, reservoir body 48 comprises between about 50 weight % and about 70 weight % PVP, such as about 60 weight % PVP. Reservoir body 48 may comprise two or more hydrophilic materials that are selected to optimize the loading of therapeutic agent 56, the stability of therapeutic agent 56, and the release rate of therapeutic agent 56 from reservoir body 48. In one example, reservoir body 48 may comprise both PVP and glycerol, such as between about 50 weight % and about 70 weight % PVP, for example about 60 weight % PVP, and between about 20 weight % and about 40 weight % glycerol, for example about 29 weight % glycerol.

Other biocompatible polymers 54 that may be used in reservoir body 48 may include, for example, a polyurethane or a silicone. In some examples, the silicone or polyurethane may be mixed with hydrophilic polymer, such as the hydrophilic polymers described above, to provide a controlled release mechanism, e.g., because the silicone or polyurethane may slow down the release of therapeutic agent 56 from reservoir 48. Various types of silicone may be used, including, for example, silicone pressure sensitive adhesive (PSA), room temperature vulcanization (curing) (RTV) silicone, liquid silicone rubber (LSR), enhanced tear resistance (ETR) silicone, or the like. Exemplary silicones include, but are not limited to, Silastic® Q-7-4850 LSR, available from Dow Corning, Corp., Midland, Mich.; Silastic® MDX4-4210, available from Dow Corning, Corp., Midland, Mich.; Q7-4735, Q7-4750, and Q7-4765 ETR silicones, available from Dow Corning, Corp., Midland, Mich.; NuSil MED-1137 and NuSil MED-200 RTV silicones, available from NuSil Technology, LLC, Carpinteria, Calif.; Rehau SI-1511 RTV silicone, available from Rehau Co., Leesburg, Va.; Silastic® MDX7-4502, BIO-PSA 7-4501, BIO-PSA 7-4402, BIO-PSA 7-4502, BIO-PSA-4602, 7-9800 SSA, and MG7-9850 PSA silicones, available from Dow Corning, Corp., Midland, Mich. In some examples, the at least one therapeutic agent may be mixed into the silicone or a constituent of the silicone, prior to curing, while in other embodiments, the at least one therapeutic agent may be mixed into the silicone subsequent to curing of the silicone.

In other examples, polymer 54 may comprise another PSA, such as an acrylic PSA, a polyisobutylene PSA, a polyurethane PSA, a cyanoacrylate PSA, a PLGA-based PSA, or the like. In examples such as these, the at least one therapeutic agent may be mixed into the PSA. Forming reservoir 26 from a PSA may result in a higher release rate (elution rate) of the therapeutic agent than from a polymer with a higher cross-link density, because the PSA has little or no cross-linking.

In other examples, the biocompatible polymer 54 may also include a biodegradable or bioabsorbable polymer, such as, for example, collagen, poly(lactic-co-glycolic acid) (PLGA), poly(lactic acid) (PLA), poly(glycolic acid) (PGA), polyethylene glycol (PEG), PEG stearate, poly(ethylene oxide) (PEO), poly(ethylene co-vinyl acetate), poly(ortho ester) (POE), poly(ε-caprolactone) (PCL), poly(dioxanone), polyglyconate, hyaluronic acid, gelatin, fibrin, fibrinogen, cellulose, starch, cellulose acetate, polyvinylpyrrolidone (PVP), a poly(ethylene oxide)/poly(propylene oxide) copolymer (PEO-PPO), a polyethylene-polypropylene glycol copolymer, poly(ethylene vinyl acetate), poly(hydroxybutyrate-co-valerate), polyanhydride, poly(glycolic acid-co-trimethylene carbonate), polyphosphoester, polyphosphoester urethane, a poly(amino acid), a cyanoacrylate, poly(trimethylene carbonate), poly(iminocarbonate), a copoly(ether-ester) such as PEO/PLA, a polyalkylene oxalate, a polyphasphazene, a polyarylate, a tyrosine-based biodegradable or bioabsorbable polymer, poly hydroxyalkanoate (PHA), poloxamers, polymethyl vinyl ether/maleic anhydride, a sugar ester, or the like. The biodegradable or bioabsorbable polymer may degrade and be absorbed by the body of patient 12 over time after implantation of reservoir 26 in the body of patient 12. This may be advantageous because it may ensure that substantially all the therapeutic agent is released from reservoir body 48, which may reduce risk of the growth or development of organisms that are resistant to the therapeutic agent. Further, absorption of the polymer 54 of reservoir body 48 over time may remove a site at which bacteria can grow.

Regardless of the particular polymer from which reservoir body 48 is formed, reservoir body 48 may include other components that may influence the properties of reservoir body 48. For example, reservoir body 48 may include an additive that influences the release rate of the antimicrobial from reservoir body 48, such as a plasticizer or another excipient. In another example, a surfactant may be added to reservoir body 48, which may allow for higher loading of therapeutic agent 56. A plasticizer or excipient may affect the viscosity of the polymer in reservoir body 48, which may in turn affect the release rate of the at least one antimicrobial. Thus, incorporation of a plasticizer or excipient may be one manner in which the time over which the antimicrobial is released from reservoir body 48 is affected. In some examples, the additive may swell or dissolve in biological fluids present in the body of patient 12, which may affect the release rate of the antimicrobial. Exemplary additives that influence the release rate of therapeutic agent 56 from reservoir body 48 may include, for example, poly(acrylic acid), poly(methacrylic acid), poly(vinylpyrolidone), a sugar ester, macrogol 15 hydroxystearate (IV), poly(lactic acid), lactic acid, glycerol, poly(ethylene glycol) (PEG), methyl polyethylene glycol (methyl PEG), poly(glycolic acid), poly(ε-caprolactum), polysorbate 80 (polyoxyethylene (20) sorbitan monooleate), polysorbate 20 (polyoxyethylene (20) sorbitan monolaurate), salts such as KCl, cationic surfactants, anionic surfactants, natural surfactants, or the like. Exemplary surfactants include, but are not limited to, sodium dodecyl sulfate (SDS), sodium stearate, sucrose stearate, stearyl alcohol, glycerol monostearate, mannitol, sodium laureth sulfate, sodium lauryl sulfate, triton X 100, sorbitol, fructose, chitosan, hyaluronic acid, alginate, and trimethyldodecylammonium (TMDA). As another example, reservoir body 48 may include fumed silica. Fumed silica may increase polymer integrity, such as integrity of a silicone PSA, and may also facilitate faster release of therapeutic agent 56. In some examples, the additive that influences the release rate of therapeutic agent 56 from reservoir 26 may constitute less than approximately 1 weight percent (wt. %) of reservoir body 48.

In some examples, polymer 54 of reservoir body 48 may be biodegradable or bioabsorbable such that it may be absorbed by the body of patient 12 after implantation of reservoir 26. In other embodiments, reservoir body 48 may not be biodegradable and may remain in the body of patient 12 after implantation.

The at least one therapeutic agent 56 of reservoir body 48 may include any type of agent that may be desirable for the patient and may include any therapeutic agent that is capable of exerting a therapeutic or prophylactic effect for a patient. Therapeutic agent 56 may comprise small molecule drugs, peptides, proteins, oligonucleotides, and the like. Examples of the types of therapeutic agents that may be delivered from reservoir 26 include, but are not limited to antiproliferative agents or derivatives and analogs thereof, antineoplastic agents, anti-inflammatory agents, antiplatelet agents, anticoagulant agents, antifebrin agents, antithrombin agents, antimitotic agents, anti-infective agents such as antibiotic, antimicrobial, or antiviral agents, antiallergic agents, antioxidant agents, analgesic agents and analgesic combinations, anesthetic agents, anticonvulsant agents, antipruritic agents, antipyretic agents, antispasmodic agents including gastrointestinal and urinary, sympathomimetric agents, immunosuppressive agents, muscle relaxants, parasympatholytic agents, parasympathomimetric agents, sedatives and tranquilizers. In some examples, therapeutic agent 56 may comprise an agent for the treatment of a specific disease or condition, such as anorexic agents, antiarthritic agents, antiasthmatic agents, antidepressants, antidiabetic agents, antidiarrheal agents, antihistamines, antimigraine preparations, antimotion sickness preparations, antinauseant agents, antineoplastic agents, antiparkinsonism agents, antipsychotic agents, anticholinergic agents, xanthine derivatives, cardiovascular preparations including calcium channel blockers, beta-blockers, antiarrythmics, and antihypertensives, diuretic agents, and vasodiloators, including general, coronary, peripheral and cerebral, central nervous system stimulants, cough and cold preparations, decongestants, diagnostic agents, hormones, hypnotics, and psychostimulant agents.

In one example, therapeutic agent 56 comprises an antimicrobial agent such as an antibiotic such as a tetracycline (e.g., minocycline, doxycycline), a rifamycin (e.g., rifampin, rifaximin, rifapentine, rifabutin), a macrolide (e.g., erythromycin), a penicillin (e.g., nafcillin), a cephalosporin (e.g., cefazolin), another beta-lactam antibiotic (e.g., imipenem, aztreonam) an aminoglycoside (e.g., gentamicin), a glycopeptide (e.g., vancomycin, teicoplanin), a quinolone (e.g., ciprofloxacin), fusidic acid, trimethoprim, metronidazole, mupirocin, a polene (e.g., amphotericin B), an azole (e.g., fluconazole) and a beta-lactam inhibitor (e.g., sulbactam), tigecycline, daptomycin, clindamycin, or another fluoroquinolone, bacitracin, neomycin, an antiseptic, an antimicrobial peptide, a quaternary ammonium, or the like. In some examples, the therapeutic agent may be provided in a salt form, e.g., minocycline HCl, gentamicin crobefate, or gentamicin sulfate. In some examples, two or more therapeutic agents may be selected to efficaciously prevent or treat any infection present proximate to the implant location of ICD 16, e.g., infection in the pocket in which ICD 16 is implanted. For example, one combination of therapeutic agents that may be utilized is minocycline and rifampin.

Reservoir body 48 may comprise additives to enhance or protect properties of polymer 54 or therapeutic agent 56. For example, reservoir body 48 may also include an antioxidant that may reduce or substantially prevent oxidation of therapeutic agent 56. Exemplary antioxidants include, but are not limited to, monofunctional hindered phenolic antioxidants, such as butylated hydroxyl toluene (BHT), vitamin E, vitamin A, vitamin C, or those available under the trade designation Ciba® Irganox® 1076 or Ciba® Irganox® 1010, from BASF, Florham Park, N.J. In some examples, reservoir 26 may include between approximately 0.1 wt. % and approximately 2 wt. % antioxidant. In some example, polymer 54 of reservoir body 48 may be combined with dispersion agents such as phospholipids, ethylene glycol palmitostearate, glycerin monostearate, macrogol hydroxystearate. In other examples, reservoir body 48 may comprise a humectant, such as glycerol, which may increase the solubility of therapeutic agent 56 and/or effect the activity time of therapeutic agent 56. Glycerol may also be used as a dispersion agent for therapeutic agent 56 and may also serve as a plasticizer for the agent-loaded polymer 54. In some examples, glycerol may provide a putty-like composition that may be more easily processed into a desired form factor. Other humectants that may be used include propylene glycol, glycerol triacetate, polyethylene glycol, pluonics, such as a PEG-PPG-PEG pluonic or PPG-PEG-PPG pluonic, sodium lactate, butylene glycol, polydextrose, xylitol, triacetin, and triethanolamine.

Reservoir body 48 may be made by a variety of techniques. For example, reservoir body 48 may comprise a mixture of one or more polymers 54 and one or more therapeutic agents 56, wherein the resulting mixture is formed into the desired shape of reservoir body 48. In one example, as described above, polymer 54 of reservoir body 48 comprises a biocompatible hydrophilic polymer or monomer, such as PVP, glycerol, PEG, PAA, PLA, or polycaprolactam, or a mixture of two or more biocompatible hydrophilic polymers or monomers, such as a combination of PVP and glycerol, with therapeutic agent 56, such as an antimicrobial agent, mixed therein. In one example, reservoir body 48 comprises a mixture of between about 50 weight % and about 70 weight % PVP, such as about 60 weight % PVP, between about 20 weight % and about 40 weight % glycerol, such as about 29 weight % glycerol, and between about 5 weight % and about 15 weight % of one or more therapeutic agents 56, such as about 11 weight % of one or more therapeutic agents 56. In one example, therapeutic agent 56 in reservoir body 48 comprises two antimicrobial agents, such as minocycline HCl and Rifampin, for example the 11 weight % therapeutic agent 56 of the previous example may be divided between about 4 weight % Minocycline HCl and about 7 weight % Rifampin. In one example, the mixture that forms reservoir body 48 is mixed, such as with a speed mixer. In one example, the mixture is mixed at about 3000 RPM with a speed mixer, such as with a DAC-150 SpeedMixer® provided by FlackTek Inc. of Landrum, S.C., for about five minutes to ensure that the components are thoroughly mixed to form a generally homogenous mixture. After mixing, the composition may be formed into the desired shape of reservoir body 48. In one example, the mixed composition is formed into a film, for example by pressing the material into a flat cavity mold. The film may be cut, such as with a punch die, into the desired shape of reservoir body 48.

In other examples, reservoir body 48 may comprise, at least in part, a silicone or another polymer formed from two or more constituent parts. The silicone may be used in addition to the hydrophilic polymer 54, such as PVP and/or glycerol described above or in place of the hydrophilic polymer 54. The hydrophilic polymer 54 may be mixed in a first constituent of the silicone, and therapeutic agent 56 may be mixed in a second constituent, wherein the second constituent may be added to the first constituent to initiate reaction of the constituents to form the silicone. In other examples, the hydrophilic polymer 54 (if present) and therapeutic agent 56 may each be mixed with the same constituent, e.g. with either the first constituent or the second constituent, before mixing the first and second constituents together. In still other examples, the first and second constituents may be mixed with each other, and then hydrophilic polymer 54 (if present) and therapeutic agent 56 may be mixed into the mixture of the first and second constituents. The hydrophilic polymer 54 (if present), therapeutic agent 56, and the constituents may be mixed using a variety of mixers, including, for example, a single-screw or twin-screw extruder, a Brabender mixer, a static mixer, an adhesive dispenser, or the like. The mixture of the two constituents, the at least one therapeutic agent 56, and the hydrophilic polymer 54 (if present) may then be formed to a desired shape, which may correspond, for example, to the shape of reservoir 26 (e.g., a disk) or may be another shape, such as a sheet from which reservoir 26 is later cut or otherwise formed. The mixture may be formed to the desired shape by injection molding, compression molding, transfer molding, casting, solvent dispersion followed by casting, spraying, extruding, painting, or the like. Finally, the mixture may be cured to allow the two constituents to react and form the silicone. In some examples, the uncured silicone including therapeutic agent 56 and hydrophilic polymer 54 (if present) may be deposited onto a release liner and passed through a furnace to effect or hasten cure of the silicone. The cured polymer and release liner may then be cut or stamped into the shape of reservoir body 48, packaged in a foil package, and sterilized, as described above, in order to prepare reservoir body 48 for application of outer coating 50.

In other examples, reservoir body 48 may include at least two therapeutic agents 56, wherein each therapeutic agent 56 may dissolve more effectively in a different solvent. Reservoir body 48 may be formed by dissolving polymer 54 and a first of the at least two therapeutic agents 56 in a first solvent, and dissolving a second of the at least two therapeutic agents 56 in a second solvent. The two solutions may then be mixed to produce a substantially homogeneous mixture including polymer 54, the first and second therapeutic agents 56, and the two solvents. The solvents may then be evaporated, leaving the dried polymer 54 having the at least two therapeutic agents 56 mixed therein. In other examples, the first therapeutic agent 56 may be mixed in a first solvent, the second therapeutic agent 56 may be mixed in a second solvent, and polymer 54 may be mixed in a third solvent. The third solvent may be the same as the first solvent or the second solvent, or may be different from each of the first and second solvents.

Reservoir body 26 is enclosed by an outer coating 50. At least a portion of outer coating 50 comprises a rate-controlling membrane 52 configured to provide a predetermined release rate of therapeutic agent 56 through rate-controlling membrane 52. In some examples, rate-controlling membrane 52 provides the predetermined release rate by being configured to provide a predetermined porosity to rate-controlling membrane 52, as described in more detail below. In other examples, rate-controlling membrane 52 may provide the predetermined release rate by comprising a material with a diffusion rate or permeability of therapeutic agent 56 that provides for the predetermine release rate.

In one example, shown in FIG. 2, a portion of outer coating 50 comprises a sheath layer 60, which may or may not be permeable to therapeutic agent 56, while the remainder of outer coating 50 comprises rate-controlling membrane 52 that is permeable to therapeutic agent 56. The percentage of the surface area of reservoir body 48 that may be covered by a rate-controlling membrane 52 that is permeable to therapeutic agent 56 may depend on the desired rate at which therapeutic agent 56 is to be released into patient 12. For example, one method of reducing the release rate of therapeutic agent 56 is to reduce the percentage of reservoir body 48 that is encased by rate-controlling membrane 52 that is permeable to therapeutic agent 56, with the remainder of outer coating 50 comprising a non-permeable sheath layer 60. In another example, shown in FIG. 3, the entirety of outer coating 50 comprises a rate-controlling membrane 52 that is permeable to therapeutic agent 56. As described in more detail below, rate-controlling membrane 52 may be configured to control the rate of release of therapeutic agent 56, such as by controlling the formulation of rate-controlling membrane 52 in order to control porosity and pore size within rate-controlling membrane 52.

Figure 4A:
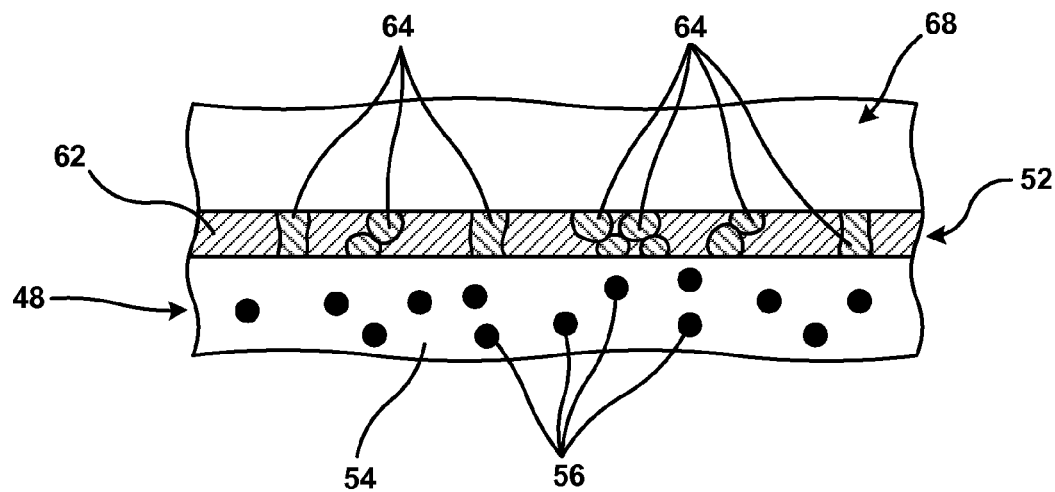
FIG. 4A is a cross-sectional conceptual diagram illustrating a rate-controlling membrane of an example of a reservoir for the delivery of a therapeutic agent, wherein the rate-controlling membrane comprises a biosoluble material for the formation of pores.
Figure 4B:
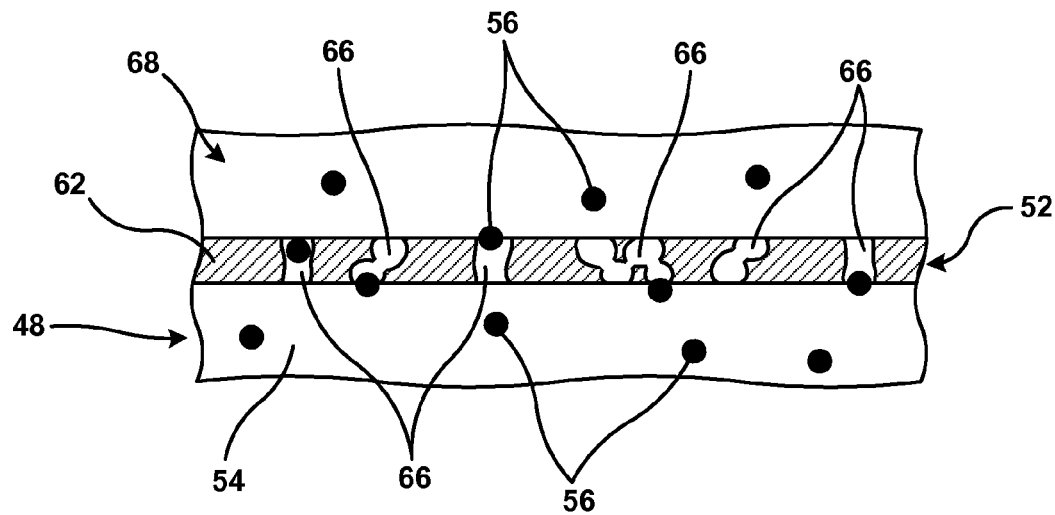
FIG. 4B is a cross-sectional conceptual diagram illustrating the rate-controlling membrane of FIG. 4A after dissolution of the biosoluble material to form pores.
Figure 5:
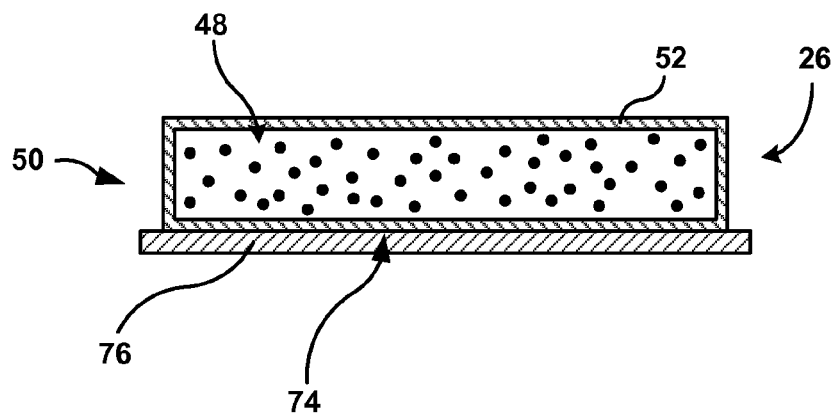
FIG. 5 is a cross-sectional diagram illustrating the example reservoir of FIG. 3 adhered to a release liner.

In one example, shown in FIGS. 4A and 4B rate-controlling membrane 52 comprises a biocompatible polymer 62 that is configured to provide a predetermined permeability for therapeutic agent 56 through rate-controlling membrane 52. In some examples, polymer 62 may comprise substantially the same polymer as polymer 54 of reservoir body 48, wherein polymer 62 of rate-controlling membrane 52 is made by different processes so that the predetermined release rate of therapeutic agent 56 is achieved, such as by molding polymer 54 of reservoir body 48, and electrospinning polymer 62 of rate-controlling membrane 52.

In one example, polymer 62 comprises a biocompatible hydrophobic polymer 62 that is configured to impart a predetermined porosity to rate-controlling membrane 52 such that pores 66 are formed in rate-controlling membrane 52 (FIG. 4B). The porosity permits passage of therapeutic agent 56 out of reservoir body 48 and through rate-controlling membrane 52 through pores 66. In one example, pores 66 may be formed in hydrophobic polymer 62 of rate-controlling membrane 52 through the dissolution of a biosoluble material 64, such as a hydrophilic excipient, that is loaded into the hydrophobic polymer 62. As shown in FIG. 4A, loaded biosoluble material 64 is dispersed through hydrophobic polymer 62 such that it is exposed to tissue and fluid 68 within patient 12 after implantation. The fluid and/or tissue dissolves biosoluble material 64 so that pores 66 are formed in hydrophobic polymer 62, as shown in FIG. 4B. After pores 66 have been formed in hydrophobic polymer 62, therapeutic agent 56 that is stored within reservoir body 48 can diffuse through pores 66 and be released from reservoir 26 into the tissue or fluid 68 of patient 12.

In some examples, biosoluble material 64 loaded into polymer 62 of rate-controlling membrane 52, such as a hydrophilic excipient, may comprise at least one of polyvinylpyrolidone (PVP), polyacrylic acid (PAA), polymethacrylic acid, poly(lactic-co-glycolic acid) (PLGA), polylactic acid (PLA) or its monomer lactic acid, polyethylene glycol (PEG), polycaprolactam, methyl polyethylene glycol (methyl PEG), poly(glycolic acid) (PGA), poly(ethylene oxide) (PEO), poly (ortho ester) (POE), poly(ϵ-caprolactone) (PCL), poly(dioxanone), polyglyconate, a polyvinylalcohol, a poly(ethylene oxide)/poly(propylene oxide) copolymer (PEO-PPO), poly (ethylene vinyl acetate), poly(hydroxybutyrate-covalerate), polyanhydride, poly(glycolic acid-co-trimethylene carbonate), polyphosphoester, polyphosphoester urethane, a poly (amino acid), a cyanoacrylate, poly(trimethylene carbonate), poly(iminocarbonate), a copoly(ether-ester) such as PEO/PLA, a polyalkylene oxalate, a polyphasphazene, a polyarylate, a tyrosine-based biodegradable or bioabsorbable polymer, poly hydroxyalkanoate (PHA), a sugar ester, hyaluronic acid, macrogol 15 hydroxystearate (IV), glycerol, polyglycolic acid, poly($\epsilon$-caprolactum), polysorbate 80 (polyoxyethylene (20) sorbitan monooleate), polysorbate 20 (polyoxyethylene (20) sorbitan monolaurate), collagen, gelatin, fibrin, fibrinogen, cellulose, starch, cellulose acetate, or the like.

In some examples, the porosity of rate-controlling membrane 52 may be provided by solvent electrospinning a biodegradable polymer, such as poly(lactic-co-glycolic acid) (PLGA), collagen or a polyurethane foam. The biosoluble material 64 may also comprise water soluble and/or resorbable materials, such as, for example, salts, such as sodium chloride, sodium bicarbonate, sodium lactate, ammonium alginate, sugars, such as sucrose, polydextrose, polysaccharide, or humectants, such as butylene glycol, triacetin and triethanolamine.

Pores 66 may be formed in rate-controlling membrane 52 by other means, such as via processing techniques of hydrophobic polymer 62, for example laser drilling pores 66 in hydrophobic polymer 62, molding or casting hydrophobic polymer 62 so that pores 66 are formed, or by selective curing or etching of hydrophobic polymer 62 so that pores 66 are formed.

As described above, in some examples, rate-controlling membrane 52 may only form a portion of outer coating 50, with the remainder of outer coating 50 comprising a sheath layer 60 that may or may not be permeable to therapeutic agent 56. In some examples, sheath layer 60 may comprise a biocompatible hydrophobic polymer 72 similar to polymer 62 of rate-controlling membrane 52. In some examples, hydrophobic polymer 72 of sheath layer 60 is not permeable to therapeutic agent 56 or fluids within patient 12. In some examples, hydrophobic polymer 72 of sheath layer 60 is the same polymer as hydrophobic polymer 62 of rate-controlling membrane 52, except that sheath layer 60 need not have pores such that polymer 72 of sheath layer 60 does not need to be configured to form pores in hydrophobic polymer 72.

In some examples, the biocompatible hydrophobic polymer 62 of rate-controlling membrane 52 or biocompatible hydrophobic polymer 72 of sheath layer 60 (if present) may be biodegradable or bioabsorbable, such that outer coating 50 breaks down over time after being implanted in patient 12. Similarly, polymer 54 of reservoir body 48 may also be biodegradable or bioabsorbable. Biodegradable or bioabsorbable polymers 54, 62, 72 may permit outer coating 50, including rate-controlling membrane 52 and sheath layer 60, and reservoir body 48 to be absorbed by the body of patient 12 after implantation of reservoir 26. In other embodiments, the components of reservoir 26 may not be biodegradable and may remain in the body of patient 12 after implantation. A biodegradable or bioabsorbable reservoir 26 may facilitate release of substantially all of therapeutic agent 56 after an extend period of time, which may reduce the risk of bacteria developing resistance to therapeutic agent 56. Biodegradable polymers 54, 62, 72 may also mitigate or prevent growth of bacteria on reservoir 26 after therapeutic agent 56 has eluted from reservoir 26. For example, biodegradable polymers 54, 62, 72 may break down over time after being implanted in patient 12. In some examples, each biodegradable polymer 54, 62, 72, may comprise collagen, poly(lactic-co-glycolic acid) (PLGA), poly(lactic acid) (PLA), poly(glycolic acid) (PGA), poly(ethylene oxide) (PEO), poly(ortho ester) (POE), poly($\epsilon$-caprolactone) (PCL), poly(dioxanone), polyglyconate, hyaluronic acid, gelatin, fibrin, fibrinogen, cellulose, starch, cellulose acetate, polyvinylpyrrolidone (PVP), a poly (ethylene oxide)/poly(propylene oxide) copolymer (PEO-PPO), poly(ethylene vinyl acetate), poly(hydroxybutyrate-covalerate), polyanhydride, poly(glycolic acid-co-trimethylene carbonate), polyphosphoester, polyphosphoester urethane, a poly(amino acid), a cyanoacrylate, poly(trimethylene carbonate), poly(iminocarbonate), a copoly(ether-ester) such as PEO/PLA, a polyalkylene oxalate, a polyphosphazene, a polyarylate, a tyrosine-based biodegradable or bioabsorbable polymer, poly hydroxyalkanoate (PHA), a sugar ester, or the like.

In other examples, the biocompatible polymer 62, 72 of rate-controlling membrane 52 and sheath layer 60 is not biodegradable and may remain adhered to ICD 16 indefinitely after ICD 16 has been implanted in patient 12. For example, polymer 62, 72 may include silicone or polyurethane. A silicone polymer 62, 72 may comprise a silicone pressure sensitive adhesive (PSA), a room temperature vulcanization (curing) (RTV) silicone, an enhanced tear resistance (ETR) silicone, a liquid silicone rubber (LSR), or the like. For example, an RTV silicone, an ETR silicone, or a LSR may be produced by reacting a first constituent and a second constituent to form the RTV silicone, the ETR silicone, or LSR. The first and second constituents may then react or cure to produce the cured silicone and be formed to the desired form factor of outer coating 50, including rate-controlling membrane 52. Exemplary silicones that may be used as polymer 62, 72 include, but are not limited to, Silastic® Q-7-4850 LSR, available from Dow Corning, Corp., Midland, Mich.; Silastic® MDX4-4210, available from Dow Corning, Corp., Midland, Mich.; Q7-4735, Q7-4750, and Q7-4765 ETR silicones, available from Dow Corning, Corp., Midland, Mich.; NuSil MED-1137 and NuSil MED-200 RTV silicones, available from NuSil Technology, LLC, Carpinteria, Calif.; Rehau SI-1511 RTV silicone, available from Rehau Co., Leesburg, Va.; Silastic® MDX7-4502, BIO-PSA 7-4501, BIO-PSA 7-4402, BIO-PSA 7-4502, BIO-PSA-4602, 7-9800 SSA, and MG7-9850 PSA silicones, available from Dow Corning, Corp., Midland, Mich.

In other examples, a silicon polymer 62, 72 may include an RTV silicone that is formed from one component that cures at room temperature to form the cured silicone 62, 72. The silicone may be cured by exposure to atmospheric moisture, e.g., water vapor. Some such RTV silicone systems may include acetoxy, methoxy or ethoxy functional groups that react with water vapor and liberate acetic acid, methanol, or ethanol, respectively, during the curing process. As the RTV silicone cures, the mixture may be formed to the desired form factor of reservoir 26.

In some examples, a silicone polymer 62, 72 may include an ETR silicone, which may be processed by milling to mix the first and second constituents of the silicone followed by curing to form the cured ETR silicone and formed into a desired form factor of reservoir 26. For example, the ETR silicone may be extruded or molded to begin the reaction of the first and second constituents and the cure of the ETR silicone, and may be formed into a desired form factor, e.g., a sheet or film, by the extrusion or molding process.

In other examples, polymer 62 of rate-controlling membrane 52 or polymer 72 of sheath layer 60 may include a pressure-sensitive adhesive (PSA). The PSA may include a silicone PSA, or may include, for example, an acrylic PSA, a polyisobutylene PSA, a polyurethane PSA, a cyanoacrylate PSA, a PLGA-based PSA, or the like. In some examples, the PSA may be delivered in a solvent. For example, a silicone PSA may be delivered as 60 weight percent (wt. %) solids (i.e., silicone) in ethyl acetate. Because PSAs may have little or no cross-linking, a rate-controlling membrane 52 including a PSA may release therapeutic agent 56 at a higher elution rate than a reservoir including a membrane comprising a cross-linked polymer (i.e., a polymer having a higher crosslink density). This may be advantageous because it facilitates a higher initial dosage of therapeutic agent 56 to the implant site.

In some examples, reservoir 26 may be adhered to outer surface 42 of housing 40 by an adhesive. In one example, illustrated in FIG. 2, a layer of adhesive 44 adheres reservoir 26 to housing surface 42. Examples of materials of adhesive 44 include a silicone PSA, an acrylic PSA, a polyurethane PSA, a cyanoacrylate PSA, a PLGA-based PSA, or polyisobutylene PSA. Adhesive 44 may be applied to surface 46 of reservoir 26 or to surface 42 of ICD housing 40 by, for example, spray coating, knife coating, air knife coating, gap coating, gravure coating, slot die coating, metering rod coating, doctor blade, or the like. In another example, illustrated in FIG. 3, an outer coating 50 of reservoir 26 comprises a pressure-sensitive adhesive (PSA), for example a polymer that makes up a portion of outer coating 50 may comprise a silicone PSA, such that reservoir 26 may be adhered to housing 40 via the PSA within outer coating 50.

In other examples, as illustrated in FIG. 3, at least a portion of outer coating 50 may comprise a PSA portion 74. In some examples, the PSA portion 74 of outer coating 50 may comprise at least a portion of rate-controlling membrane 52 so that outer coating 50 both adheres reservoir 26 to housing 40 and provides control over the release rate of therapeutic agent 56 from reservoir 26. In these examples, the PSA portion 74 may include, for example, a silicone PSA, an acrylic PSA, a polyurethane PSA, a cyanoacrylate PSA, a PLGA-based PSA, or polyisobutylene PSA.

When at least a portion 74 of outer coating 50 comprises a PSA, then reservoir 26 may be adhered directly to surface 42 of ICD housing 40 without the need of a separate adhesive layer, such as adhesive layer 44 shown in FIG. 2. FIG. 3 shows an example wherein at least the portion 74 of outer coating 50 that contacts surface 42 of housing 40 comprises a PSA polymer 62 such that reservoir 26 may be adhered to housing 40 via PSA polymer 62 of outer coating 50. As shown in the example of FIG. 3, the entirety of outer coating 50 may comprise rate-controlling membrane 52, and in one example, the entirety of rate-controlling membrane 52 may comprise a PSA polymer 62.

Regardless of whether the adhesive is a separate adhesive layer 44 applied between reservoir 26 and housing 40 (FIG. 2) or is part of outer coating 50 (FIG. 3), PSA portion 74 reservoir 26 may be disposed on a release liner 76, such as a fluoropolymer release liner, to provide a convenient article for storing, shipping, and providing reservoir 26 to the implanting clinician. In some examples, reservoir 26 disposed on release liner 76 may be packaged in a foil package or other substantially air and water impermeable package that is vacuum sealed or backfilled with an inert gas. Reservoir 26 may then be sterilized by, for example, electron beam, gamma beam, ethylene oxide, autoclaving, or the like.

As described above, rate-controlling membrane 52 is configured to allow passage of therapeutic agent 56 out of reservoir 26. In some examples, shown in FIGS. 4A and 4B, rate-controlling membrane 52 is configured to create porosity within rate-controlling membrane 52, such as through the dissolution of a biosoluble material, such as a hydrophilic biosoluble material 64, for example PVP, glycerol, PEG, PAA, PLA, or polycaprolactam, loaded into a hydrophobic polymer 62. Dissolution of biosoluble material 64 creates pores 66 within polymer 62, wherein therapeutic agent 56 may elute through pores 66.

The relative composition of biosoluble material 64 loaded within polymer 62 may be selected to provide for a desired porosity, which in turn may have a direct effect on the rate of release of therapeutic agent 56 from reservoir 26. In some examples, the relative composition (e.g. the weight percentage of rate-controlling membrane 52) of biosoluble material 64 may be selected to control the resulting porosity of rate-controlling membrane 52 in order to select a desired release rate of therapeutic agent 56. In one example, rate-controlling membrane 52 comprises between about 5 weight % and about 50 weight % biosoluble material 64, such as between about 15 weight % and about 45 weight % biosoluble material 64, for example about 35 weight % biosoluble material 64, with the remainder consisting essentially of a polymer 62, such as a hydrophilic polymer 62, for example a silicone or silicon PSA. In one example, rate-controlling membrane comprises between about 55 weight % and about 75 weight % polymer 62, for example about 65 weight % polymer 62, and between about 25 weight % and about 45 weight % biosoluble material 64, for example about 35 weight % biosoluble material 64. In one example, polymer 62 of rate-controlling membrane comprises a silicone PSA, such as Silastic® MDX7-4502, BIO-PSA 7-4501, BIO-PSA 7-4402, BIO-PSA 7-4502, BIO-PSA-4602, 7-9800 SSA, and MG7-9850 PSA silicones, available from Dow Corning, Corp., Midland, Mich., loaded with a PVP biosoluble material 64.

As noted above, the relative composition of biosoluble material 64, such as the weight percentage of biosoluble material 64 in rate-controlling membrane 52, has an effect on the porosity that results in rate-controlling membrane 52 upon the dissolution of biosoluble material 64 after implantation. In some examples, the resulting porosity of rate-controlling membrane 52, such as the porosity resulting from the dissolution of biosoluble material 64, may be between about 0.2 (e.g., about 20% void space) and about 0.5 (e.g., about 50% void space), such as between about 0.25 (e.g., about 25% void space) and about 0.45 (e.g., about 45% void space), for example about 0.35 (e.g. about 35% void space). In the example wherein polymer 62 comprises a silicone PSA and biosoluble material 64 comprises PVP, the densities of polymer 62 (silicone PSA) and biosoluble material (PVP) are approximately equal (e.g., silicone PSA has a density of about 1.1 grams per $cm^3$ and PVP has a density of about 1.18 grams per $cm^3$) such that the percent of void space is approximately equal to the weight percentage of biosoluble material 64 in polymer 62 (e.g., if rate-controlling membrane 52 is about 65 weight % silicone PSA polymer 62 and about 35 weight % PVP biosoluble material 64, then the resulting porosity would be about 0.35, or about 35% void space). As noted above, the specific desired porosity will depend on the desired release rate of therapeutic agent 56 through rate-controlling membrane 52, so for some applications a porosity of about 0.25 may be desirable, but in other applications that may result in too low of an elution rate such that a porosity of about 0.3 to about 0.35 may be desirable.

The average size of the resulting pores 66 (e.g. the average pore diameter) may affect the rate of release of therapeutic agent 56 through rate-controlling membrane 52. Therefore, in some examples the composition and/or processing of rate-controlling membrane 52 may be selected in order to achieve a desired average pore size of pores 66. For example, if biosoluble material 64 is solubilized, the resulting pore sizes may be smaller. Pore sizes may also be controlled by milling the composition with a two or three roll mill. When milling at sufficiently high forces the particles of biosoluble material 64 may be subdivided and create smaller pore sizes. Sonication and/or high shear dispersion mixing may also be used to break up agglomerates of biosoluble material 64 and create smaller particles (resulting in smaller pore sizes). Pore size may also be chosen, for example, by specifying to the raw material supplier a desired particle distribution size of biosoluble material 64 or by separating out larger or smaller particles using a sieve. Larger pore size may also be achieved by providing a higher concentrations of biosoluble material 64 when forming rate-controlling membrane 52, which may tend to produce larger pore sizes due to a higher potential for agglomeration of biosoluble material 64. In some examples, pores 66 may have a pore size range of between about 10 micrometers and about 200 micrometers, such as between about 30 micrometers and about 150 micrometers. In some examples, the average size of pores 66 may be between about 45 micrometers and about 75 micrometers, such as between about 60 micrometers and about 70 micrometers.

Reservoir 26 may include a range of thicknesses, such as between about 0.0013 cm (about 0.0005 inch or about 0.5 mils) to about 0.25 cm (about 0.100 inch or about 100 mils), for example about 0.025 cm (about 0.01 inches or about 10 mils). The thickness of reservoir 26 may affect the release rate of antimicrobial from reservoir 26, particularly as the volume of reservoir 26 adjacent to top surface 78 is depleted of antimicrobial and the antimicrobial must diffuse from an inner volume 50 of reservoir body 48 to top surface 78 to be released into the body of patient 12. In addition, the diameter of reservoir 26, e.g., if reservoir 26 is shaped generally as a circular disk 28 (FIG. 1), along with the thickness of reservoir 26, may affect the total amount of therapeutic agent 56 which is carried by the reservoir 26. In some examples, reservoir 26 may have a diameter between about 0.32 cm (about 0.125 inches) and about 10.2 cm (about 4 inches), such as between about 1.59 cm (about 0.625 inch) and about 1.9 cm (about 0.75 inch).

Although reservoir 26 has been described as being attached to housing 40 of ICD 16 by an adhesive, such as adhesive layer 44 (FIG. 2) or via an adhesive material such as a PSA in outer coating 50 (FIG. 3), in other examples, reservoir 26 may be attached to ICD 16 by other means, such as, for example, a suture or staple to connector block 27 of ICD 16 or an aperture defined in connector block 27. Connector block 27 may be formed of a polymer. In other examples, reservoir 26 may not be attached to housing 40 in any manner, and may simply be implanted in patient 12 proximate to ICD 16 (e.g., at the implant site, next to ICD 16). These methods may be advantageous when reservoir 26 includes a biodegradable polymer, because no adhesive residue will be left on a surface of housing 40. In some examples, the suture may also be biodegradable.

Figure 6:
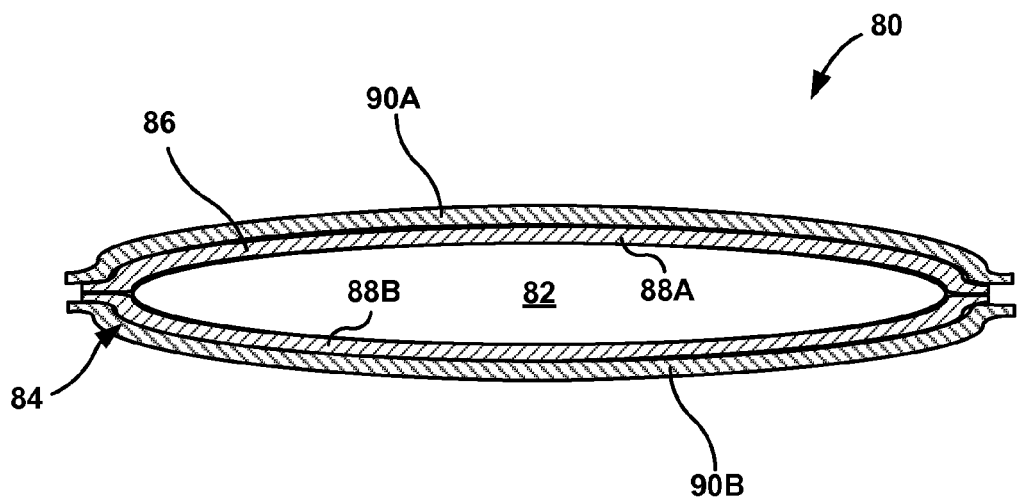
FIG. 6 is a cross-sectional diagram of another example reservoir for the delivery of a therapeutic agent.

In one example, shown in FIG. 6, a reservoir 80, which may be similar to reservoir 26, comprises a reservoir body 82 enclosed by an outer coating 84. Like reservoir body 48 of reservoir 26, reservoir body 82 may comprise a polymer, such as any of the polymers described above for reservoir body 48, and a therapeutic agent, such as any of the therapeutic agents 56 described above, although neither the polymer or therapeutic agent are shown in FIG. 6. Outer coating 84 of reservoir 80 may be similar to outer coating 50 of reservoir 26, in that at least a portion of outer coating 84 comprises a rate-controlling membrane 86 comprising a polymer configured to provide a predetermined porosity to the rate-controlling membrane 86. Outer coating 84 may be formed from two sheets or films 88A, 88B that may be laminated with reservoir body 82 to form reservoir 80. Each sheet 88A, 88B may have the same composition, or each sheet may be formed from a different composition. In one example, sheet 88A may have a first composition, for example a composition that forms rate-controlling membrane 86, while sheet 88B has a second composition, such as a composition to form a different rate-controlling membrane (e.g., a membrane configured to have a different porosity or a different average pore size from that of sheet 88A resulting in a different release rate of the therapeutic agent) or a composition to form a sheath layer that is not configured to provide a porosity.

In another example, both sheets 88A and 88B are formed from the same mixture of a polymer loaded with a biosoluble material such that sheets 88A, 88B form rate-controlling membrane 86 substantially around the entirety of reservoir body 82. If sheets 88A, 88B are to be made from the same composition, then they may be made from the same mixture of polymer and biosoluble material. In such a case, a first portion of the mixture of the polymer and biosoluble material may be used to form sheet 88A, such as by casting the mixture onto a release liner 90A using a draw knife in order to form sheet 88A. A second portion of the mixture of the polymer and the biosoluble material may be used to form sheet 88B, such as by casting the mixture onto a release liner 90B using a draw knife in order to form sheet 88B. After sheets 88A and 88B are formed, reservoir body 48 may be laminated between sheets 88A and 88B so that sheets 88A, 88B form outer coating 84. Reservoir body 82 may be laminated to sheets 88A, 88B using an adhesive. In some examples, described above, the polymer that is used to form sheets 88A and 88B comprises a PSA, such as a silicone PSA, such that reservoir body 48 may be adhered to sheets 88A and 88B via the PSA. Reservoir body 48 may be sealed between sheets 88A, 88B by sealing sheet 88A to sheet 88B, such as with an adhesive, or by welding sheets 88A, 88B together.

Figure 7A:
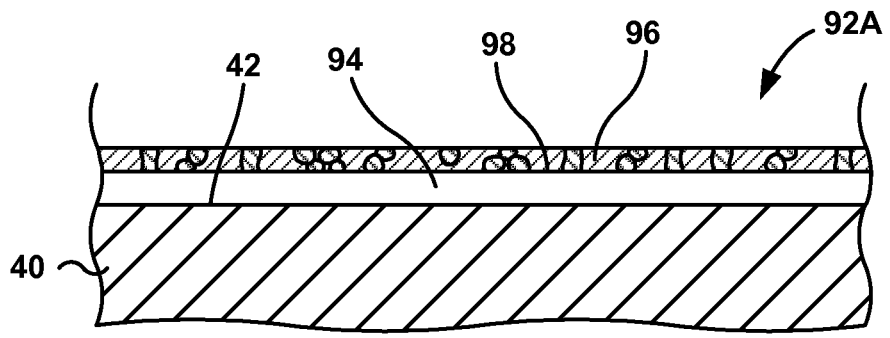
FIGS. 7A-7C are cross-sectional diagrams of example reservoirs for the delivery of a therapeutic agent comprising a composite sheet reservoir.
Figure 7B:
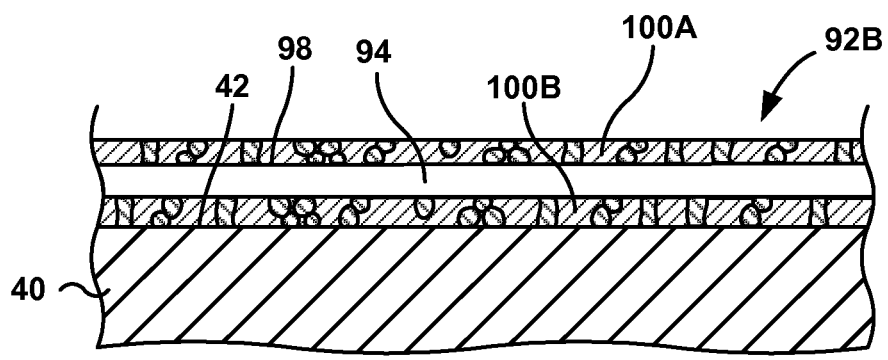
Figure 7C:
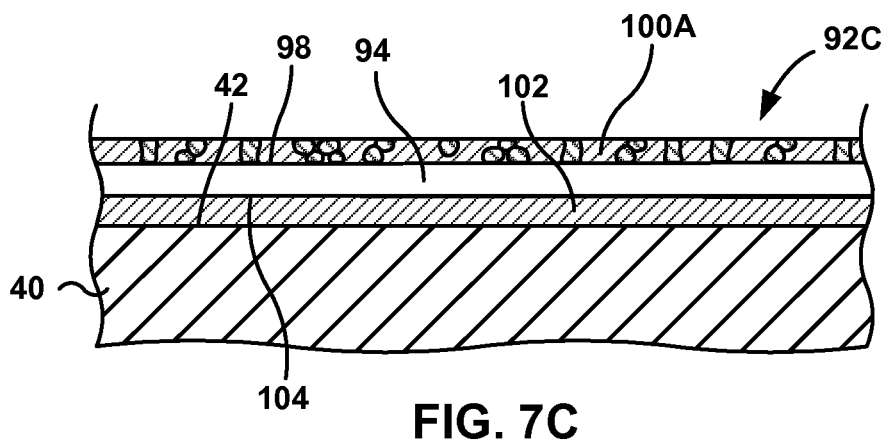

While FIG. 1 illustrates a disk 28, in other examples, a reservoir may include a different form factor. For example, FIG. 7A shows an example reservoir 92A that may comprise a composite sheet or film, e.g. a reservoir body 94 comprising a sheet or film covered by a rate-controlling membrane 96 comprising a sheet or film that is positioned at least on an outer surface 98 of reservoir body 94 opposite surface 42 of ICD housing 40, as shown in FIG. 7A. In other examples, a reservoir comprises reservoir body sheet 94 sandwiched between two rate-controlling membrane sheets 100A, 100B, as with example reservoir 92B shown in FIG. 7B, or between a rate-controlling membrane sheet 100A on an outer surface 98 of reservoir body sheet 82 and a sheath layer sheet 102 on an inner surface 104 of reservoir body sheet 94, as with example reservoir 92C shown in FIG. 7C. The composite sheet or film reservoir 92A, 92B, 92C may be adhered to housing 40, for example by adhering the composite sheet or film reservoir 92A, 92B, 92C to a single surface of housing 40, or the composite sheet or film reservoir 92A, 92B, 92C may be applied to two or more surfaces of housing 40. The composite sheet or film reservoir 92A, 92B, 92C may include a thickness similar to those described with respect to reservoir 26. Further, the composite sheet or film reservoir 92A, 92B, 92C may be manufactured by similar processes to reservoir 26, and may be packaged and sterilized similarly.

Figure 8:
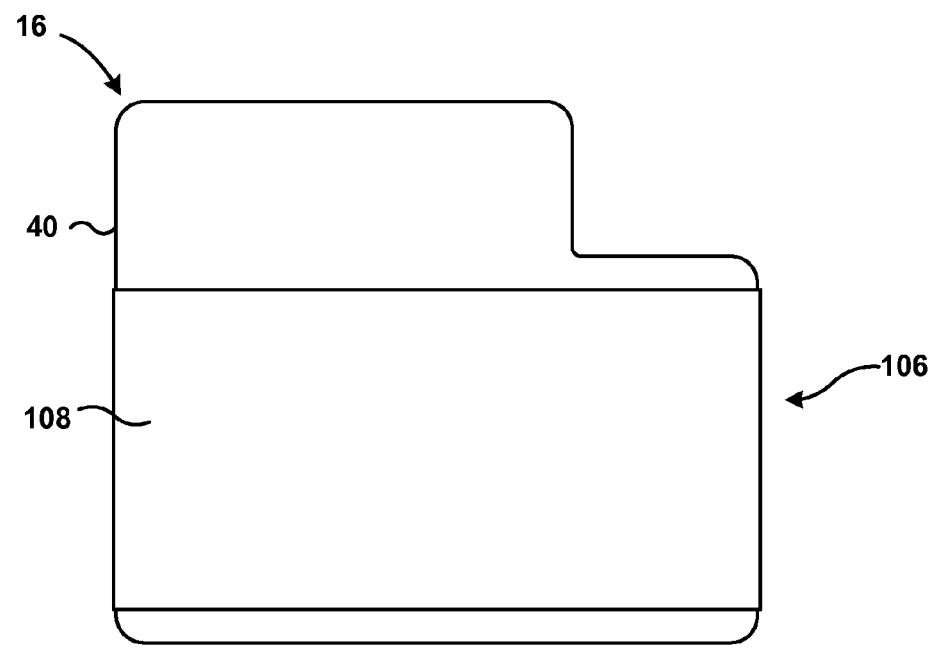
FIG. 8 is a conceptual diagram illustrating an example of an antimicrobial accessory including a sleeve attached to a housing of an implantable medical device.

Other form factors of reservoir may be used. For example, as shown in FIG. 8, an example reservoir 106 comprises a sleeve 108 that is sized and configured to fit over housing 40 of ICD 16. Although not shown in detail in FIG. 8, sleeve 108 of reservoir 106 may comprise a generally sleeve-shaped reservoir body comprising a polymer and at least one therapeutic agent and an outer covering enclosing the sleeve-shaped reservoir body, wherein at least a portion of the outer covering comprising a rate-controlling membrane configured to provide a predetermined desired porosity. In some examples, sleeve 108 is sized such that a friction fit is formed between a surface of sleeve 108 and housing 40. The friction fit may be sufficient to maintain sleeve 108 substantially in position relative to housing 40. In other examples, sleeve 108 of reservoir 106 may include a layer of adhesive applied to at least part of the surface that contacts housing 40, or a portion of sleeve may be formed of a PSA, such as a portion of a rate-controlling membrane or a sheath layer as described above with respect to reservoir 26 in FIG. 3. The adhesive, whether applied to a surface of sleeve 108 or integrated into sleeve 108, may adhere sleeve 108 to housing 40 and prevent migration of sleeve 108 relative to housing 40.

Figure 9:
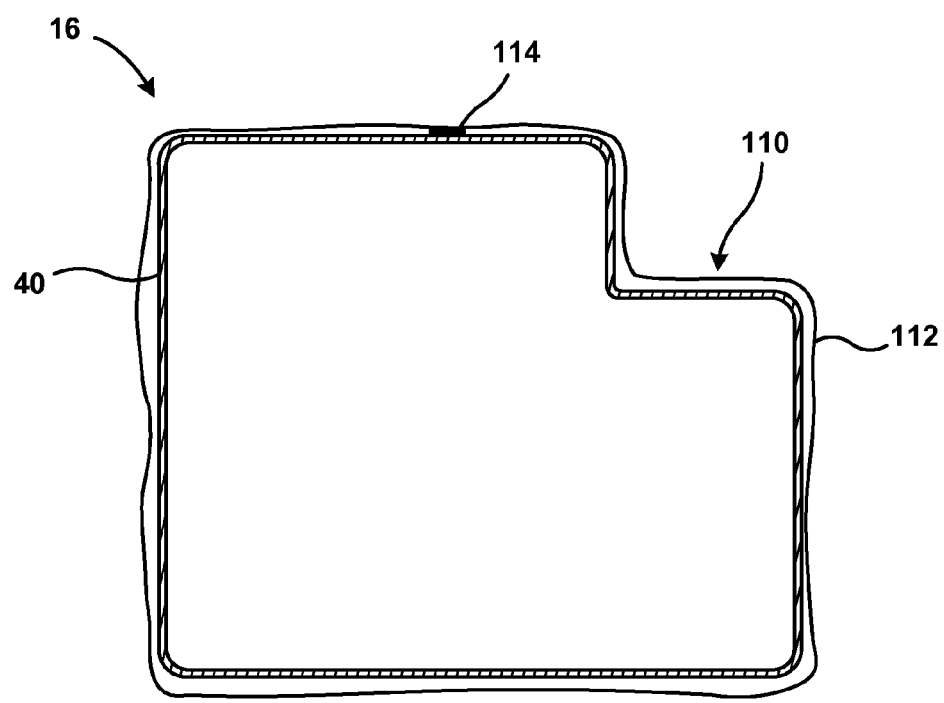
FIG. 9 is a cross-sectional diagram illustrating an example of an antimicrobial accessory including a pouch at least partially encapsulating a housing of an implantable medical device.

FIG. 9 is a cross-sectional diagram that depicts another example reservoir 110 comprising a pouch 112 that at least partially encloses housing 40. Although not shown in detail in FIG. 9, reservoir 110 may comprise a reservoir body generally shaped like a pouch, the reservoir body comprising a polymer and at least one therapeutic agent and an outer covering enclosing the pouch-shaped reservoir body, wherein at least a portion of the outer covering comprising a rate-controlling membrane configured to provide a predetermined desired porosity. In the example illustrated in FIG. 9, pouch 112 substantially fully encloses housing 40. As used herein substantially fully encloses refers to a pouch 112 to a fully encloses the housing 40, but which may define at least one aperture that permits a lead, catheter, or other probe to extend from ICD 16 and out of pouch 112. In some examples, a portion of pouch 112 may be attached to housing 40 by an adhesive 114. Adhesive 114 may also function to close an opening in pouch 112 through which ICD 16 is inserted into pouch 112. In other examples, pouch 112 simply fits around housing 40. In some examples, the opening in pouch 112 through which ICD 16 is inserted may be closed by welding, melting, or adhering two portions of pouch 112 together to form a substantially continuous pouch 112.

Figure 10:
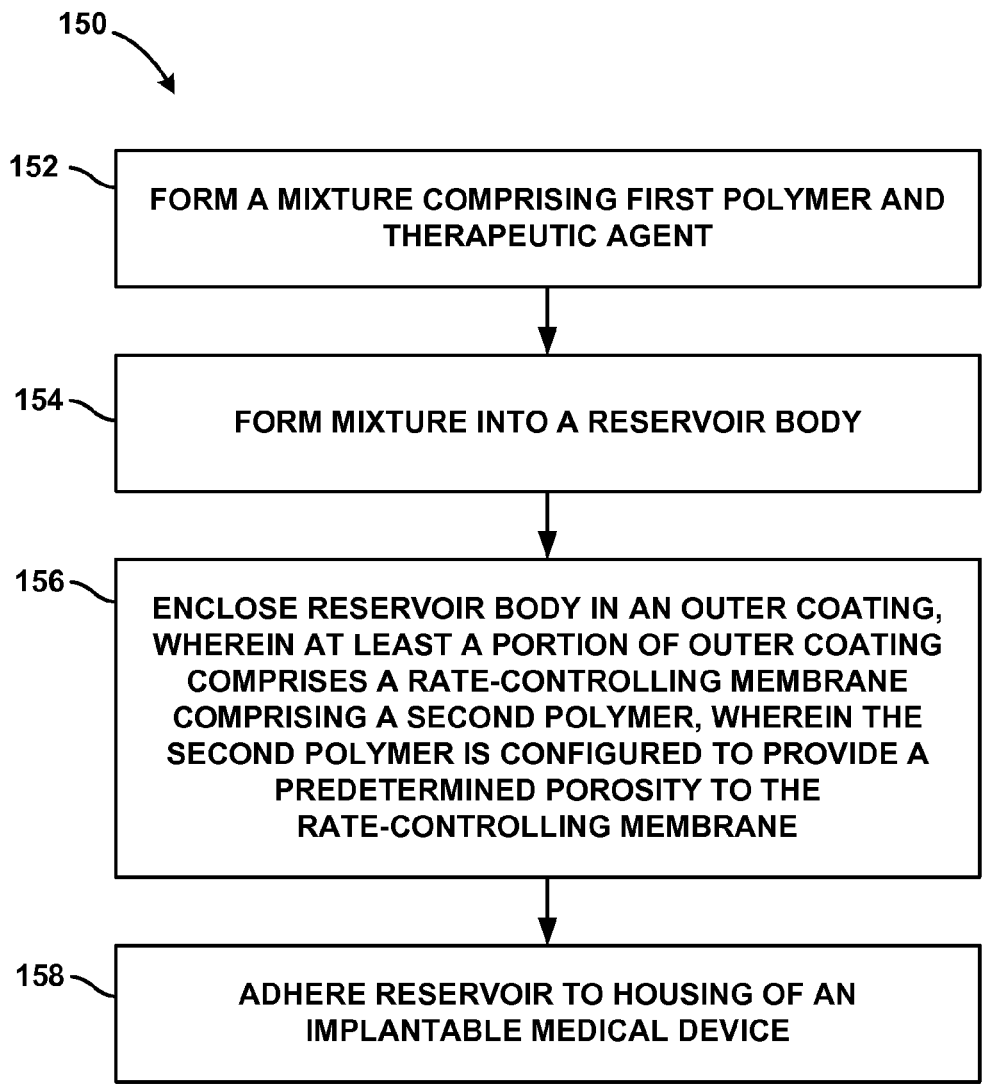
FIG. 10 is a flow diagram illustrating an example method of forming a reservoir for the delivery of a therapeutic agent.

FIG. 10 is a flow diagram of an exemplary method 150 of forming a reservoir, such as reservoir 26, for the storage and controlled release of a therapeutic agent 56. The example method 150 comprises forming a mixture comprising a first polymer 54 and a therapeutic agent 56 (152), forming the mixture into a body, such as reservoir body 48 (154), and enclosing reservoir body 48 in an outer coating 50, wherein at least a portion of outer coating 50 comprises a rate-controlling membrane 52 comprising a polymer 62, wherein polymer 62 is configured to provide a predetermined porosity to rate-controlling membrane 52 (156). In some examples, the method may also comprise adhering the reservoir to a housing of an implantable medical device (158), such as housing 40 of ICD 16.

In one example, forming the mixture of polymer 54 and therapeutic agent 56 (152) comprises speed mixing polymer 54 and therapeutic agent 56, for example in a DAC-150 SpeedMixer. In some examples, a solvent may be used to permit mixing of polymer 54, therapeutic agent 56, or both. For example, if polymer 54 comprises in part a silicone polymer, than a solvent, such as ethyl acetate, may be used to carry polymer 54 and/or therapeutic agent 56. In such a case, polymer 54, therapeutic agent 56, and the solvent may be mixed and the solvent may be driven off to leave behind the solids of polymer 54 and therapeutic agent 56.

Forming the mixture of polymer 54 and therapeutic agent 56 into a reservoir body (154) may comprise forming a desired shape using a mold or die. The desired shape may comprise a sheet, film, filament, or the like. In one example, the mixture is pressed into a flat cavity mold in order to form a thin film. The thin film may then be cut, punched, or otherwise shaped to form one or more reservoir bodies having the final desired shape, such as a disk shape of reservoir body 48 as described above. In some examples, the mixture of polymer 54 and therapeutic agent 56 may have sufficient melt strength such that the mixture may be formed into a desired shape by extruding the mixture without support, e.g. without a support structure such as a release liner or without a mold. In some examples, forming the mixture of polymer 54 and therapeutic agent 56 into reservoir body 48 (154) may comprise depositing the mixture onto a support structure, such as a release liner, to provide mechanical support for reservoir body 48 before enclosing reservoir body in outer coating 50.

Enclosing reservoir body 48 in outer coating 50 (156) may comprise forming outer coating 50 separately from reservoir body 48 and then applying outer coating 50 to reservoir body 48 in order to enclose it. In one example method, shown in FIG. 11A, enclosing a reservoir body, such as reservoir body 82 (FIG. 6) in outer coating 84 (156A) comprises forming a mixture comprising the polymer 62 and biosoluble material 64 of rate-controlling membrane 86 (160), forming the mixture into a film (162), and enclosing the reservoir body with the film (164) such that the film forms the rate-controlling membrane 86. In another example, shown in FIG. 11B, enclosing the reservoir body 82 in the outer coating 84 (156B) comprises forming a mixture comprising the polymer 62 and biosoluble material 64 of rate-controlling membrane 86 (160), forming a first film, such as sheet 88A (FIG. 6), from a first portion of the mixture (166), forming a second film, such as sheet 88B (FIG. 6), from a second portion of the mixture (168), and laminating the reservoir body 82 between the first film 88A and the second film 88B (170). Forming a film from the mixture of the polymer and biosoluble material (162, 166, 168) may comprise casting the mixture onto a release liner, such as release liner 90A, 90B, for example by using a draw knife in order to form a film or sheet 88A, 88B.

Figure 11A:
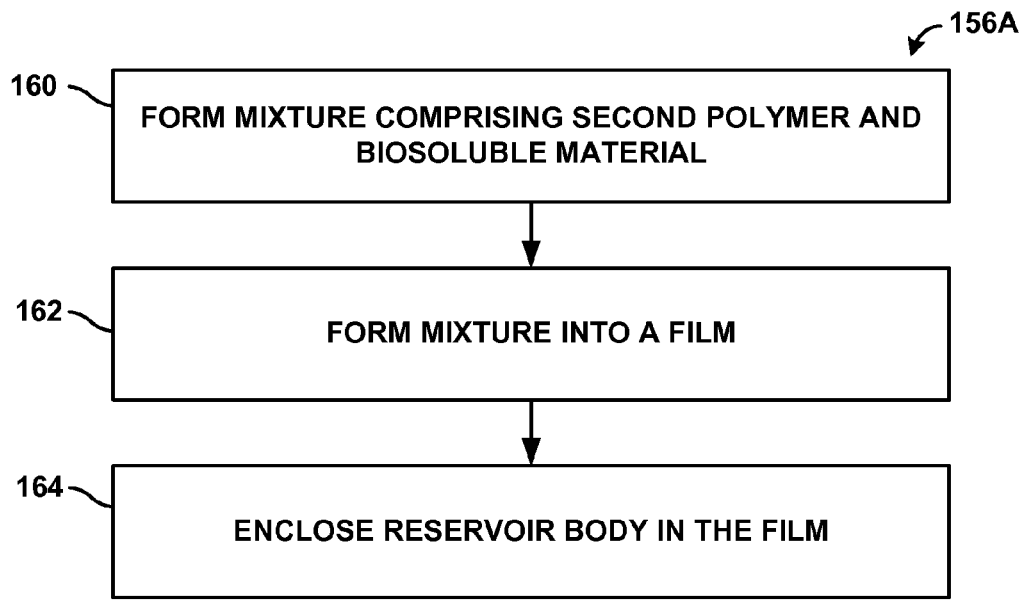
FIGS. 11A and 11B are flow diagrams illustrating example methods of enclosing a reservoir body in an outer coating comprising a rate-controlling membrane.
Figure 11B:
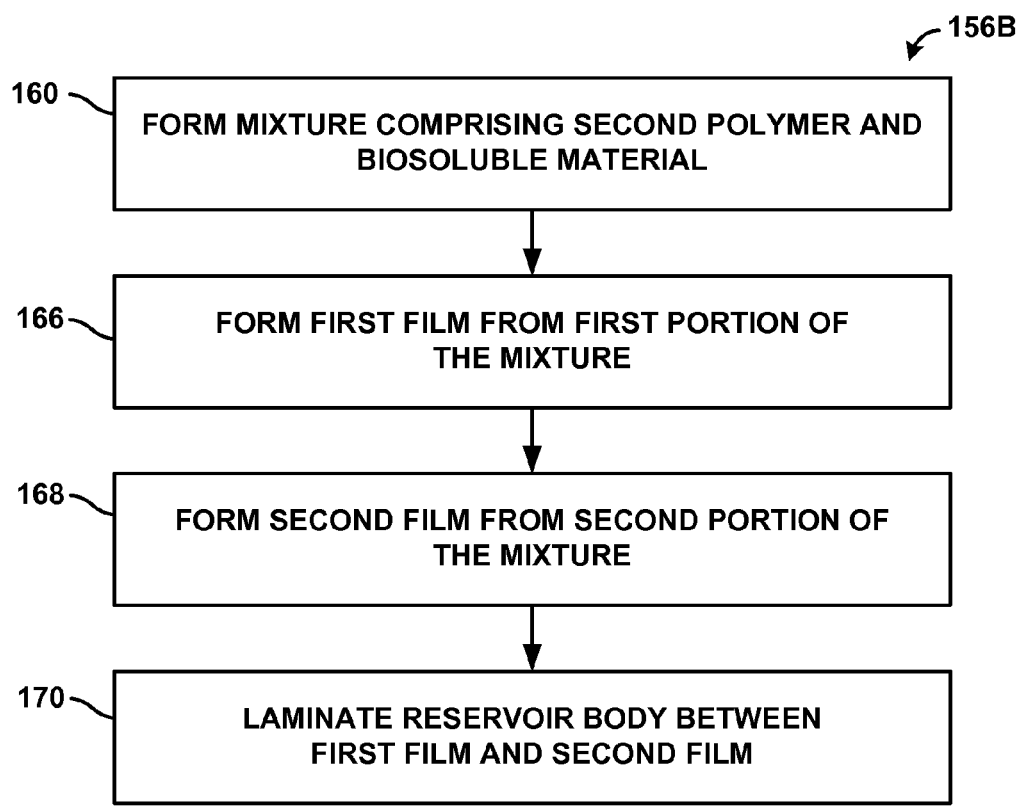

In the example method shown in FIGS. 11A and 11B, each film or sheet 88A, 88B has substantially the same composition since they are both formed from the same mixture of polymer 62 loaded with biosoluble material 64. In other examples, each sheet 88A, 88B may have a different composition, and thus may be formed from a different mixture of polymer, and if desired, biosoluble material. For example, sheet 88A may have a first composition, for example a composition that forms rate-controlling membrane 86, while sheet 88B has a second composition, such as a composition to form a different rate-controlling membrane (e.g., a membrane configured to have a different porosity or a different average pore size from that of sheet 88A resulting in a different release rate of the therapeutic agent) or a composition to form sheath layer that is not configured to provide a porosity.

Laminating the reservoir body 82 between sheets 88A, 88B (170) may comprise laminating reservoir body 82 to sheets 88A, 88B using an adhesive. In some examples, described above, the polymer 62 that is used to form sheets 88A and 88B may comprise a PSA, such as a silicone PSA, such that reservoir body 82 may be adhered to sheets 88A and 88B via the PSA. Reservoir body 82 may be sealed between sheets 88A, 88B by sealing sheet 88A to sheet 88B, such as with an adhesive, or by welding sheets 88A, 88B together.

Adhering reservoir 26 to a housing 40 of an implantable medical device 16 (158) may comprise using a separate adhesive layer 44 between reservoir 26 and housing 40, as shown in the example of FIG. 2. In some examples, at least a portion 74 of outer coating 50 may comprise a pressure sensitive adhesive (PSA) (FIG. 3), for example polymer 62 of rate-controlling membrane 52 may comprise a silicone PSA, such that adhering reservoir 26 to a housing 40 of an implantable medical device 16 (158) may be done using the pressure sensitive adhesive of outer coating 50. As described above, reservoir 26 may be adhered or attached to housing 40 by other means, such as a suture, staple, or other fastener that is used to attach reservoir 26 to housing 40.

EXAMPLE

The example reservoir 80, shown in FIG. 6, was made by the following example. A reservoir body 82 was made from a formulation of about 60 weight % polyvinylpyrrolidone, about 29 weight % glycerol, about 7 weight % rifampin, and about 4 weight % minocycline HCl. The reservoir body formulation was speed mixed using a DAC-150 SpeedMixer® provided by FlackTek Inc. of Landrum, S.C. at 2000 RPM for about 5 minutes. The resulting mixture formed a tacky, putty-like composition. The tacky, putty-like mixture was formed into a film by pressing the mixture into a flat cavity mold. The resulting film had a thickness of about 0.0254 cm (about 10 mils). A disk-shaped reservoir body 82 having a diameter of about 1.59 cm (about 0.625 inches) was cut from the film using a punch die with a hammer.

The outer coating 84 was formed from two sheets 88A, 88B of a rate-controlling membrane 86. The rate controlling membrane 86 was formed from BIO-PSA 7-4602 (lot number 0004859579) silicone PSA, available from Dow Corning, Corp., Midland, Mich., loaded with about 35 weight % of OmniPur polyvinylpyrrolidone (PVP) having molecular weight of about 40,000 (lot number 0508BL65), available from EMD Chemicals, Inc., Gibbstown, N.J. The mixture of the silicone PSA and PVP was cast onto a fluorinated release liner using a draw knife to form a film on the release liner having a wet thickness of about 0.0254 cm (about 10 mils). Two disks 88A, 88B each having a diameter of about 1.905 cm (about 0.75 inches) are cut from the film using a die punch and hammer.

The 1.59 cm (about 0.625 inch) reservoir body disk 82 was laminated between the two 1.905 cm (about 0.75 inch) rate-controlling membrane disks 88A, 88B, which formed the example reservoir 80 shown in FIG. 6. Reservoir 80 was placed in 50 milliliters of a phosphate buffer saline (PBS) solution at 37° C. and gently shaken in an orbital mixer. No immediate burst elution was observed (e.g. there was no visual assessment of a color change of the PBS solution). Within 24 hours, there was a significant amount of color change, indicating that a substantial portion of the therapeutic agent(s) (rifampin and minocycline HCl) had been eluted from reservoir 80. After 7 days, the entire amount of the therapeutic agent(s) (rifampin and minocycline HCl) had been released from reservoir 80, as determined from a visual assessment of the prototype reservoir 80. The size of pores 66 that resulted from dissolution of the PVP from rate-controlling membrane disks 88A, 88B was determined to be between about 30 micrometers and about 140 micrometers, with an average pore size of about 62 micrometers.

Various embodiments of the invention have been described. These and other embodiments are within the scope of the following claims.

The invention claimed is:

1. A system comprising:
a disc-shaped, sleeve-shaped or pouch-shaped therapeutic agent reservoir comprising a reservoir body comprising a polymer and a therapeutic agent mixed within the polymer and an outer coating enclosing the reservoir body;
wherein at least a portion of the outer coating comprises a rate-controlling membrane configured to provide a predetermined release rate of the therapeutic agent through the rate-controlling membrane; and
an implantable medical device comprising a housing, wherein the therapeutic agent reservoir is adhered to the housing of the implantable medical device and wherein the implantable medical device is an implantable cardiac device, an implantable monitoring device, an implantable neurostimulator, a cardiac or neurological lead, or an orthopedic device.

2. The system of claim 1, wherein the rate-controlling membrane comprises a second polymer for controlling release of the therapeutic agent from the reservoir body, wherein the second polymer is configured to provide the predetermined release rate to the rate-controlling membrane.

3. The system of claim 2, wherein the rate-controlling membrane further comprises a biosoluble material loaded in the second polymer of the rate-controlling membrane, wherein dissolution of the biosoluble material imparts a predetermined porosity to the rate controlling membrane, wherein the predetermined porosity provides for the predetermined release rate.

4. The system of claim 3, wherein pores formed by dissolution of the biosoluble material have a pore size range of between about 30 micrometers and about 140 micrometers.

5. The system of claim 3, wherein the biosoluble material comprises at least one of polyvinylpyrolidone (PVP), polyacrylic acid (PAA), polymethacrylic acid, poly(lactic-co-glycolic acid) (PLGA), polylactic acid (PLA) or its monomer lactic acid, polyethylene glycol (PEG), polycaprolactam, methyl polyethylene glycol (methyl PEG), poly(glycolic acid) (PGA), poly(ethylene oxide) (PEO), poly(ortho ester) (POE), poly(ε-caprolactone) (PCL), poly(dioxanone), polyglyconate, a polyvinylalcohol, a poly(ethylene oxide)/poly (propylene oxide) copolymer (PEO-PPO), poly(ethylene vinyl acetate), poly(hydroxybutyrate-covalerate), polyanhydride, poly(glycolic acid-co-trimethylene carbonate), polyphosphoester, polyphosphoester urethane, a poly(amino acid), a cyanoacrylate, poly(trimethylene carbonate), poly (iminocarbonate), a copoly(ether-ester) such as PEO/PLA, a polyalkylene oxalate, a polyphasphazene, a polyarylate, a tyrosine-based biodegradable or bioabsorbable polymer, poly hydroxyalkanoate (PHA), a sugar ester, hyaluronic acid, macrogol 15 hydroxystearate (IV), glycerol, polyglycolic acid, poly(ε-caprolactum), polysorbate 80 (polyoxyethylene (20) sorbitan monooleate), polysorbate 20 (polyoxyethylene (20) sorbitan monolaurate), collagen, gelatin, fibrin, fibrinogen, cellulose, starch, cellulose acetate, a salt, a sugar, and a humectant.

6. The system of claim 3, wherein the rate-controlling membrane comprises between about 5 weight % and about 50 weight % of the biosoluble material.

7. The system of claim 3, wherein the second polymer of the rate-controlling membrane comprises a hydrophobic polymer.

8. The system of claim 3, wherein the second polymer of the rate-controlling membrane comprises at least one of a polyurethane, a silicone pressure sensitive adhesive, a room temperature vulcanization silicone, an enhanced tear resistance silicone, and a liquid silicone rubber.

9. The system of claim 1, wherein the polymer of the reservoir body comprises at least one of polyvinylpyrrolidone (PVP), glycerol, polyethylene glycol (PEG), methyl polyethylene glycol, polyacrylic acid (PAA), polymethacrylic acid, polylactic acid (PLA), lactic acid, poly(lactic-co-glycolic acid) (PLGA), polycaprolactam, poly(trimethylene carbonate) (PMTC), chitosan, sucrose acetate isobutyrate (SAIB), polyhydroxylalkanoate (PHA), polyhydroxybutyrate (PHB), carboxymethylchitosan-oxidized starch, poloxamers, polymethyl vinyl ether/maleic anhydride, a polyethylene glycol-polypropylene glycol-polyethylene glycol (PEG-PPG-PEG) pluonic, and a polypropylene glycol-polyethylene glycol-polypropylene glycol (PPG-PEG-PPG) pluonic.

10. The system of claim 1, wherein the outer coating comprises a pressure sensitive adhesive, wherein the therapeutic agent reservoir is adhered to the housing of the implantable medical device by the pressure sensitive adhesive.

11. The system of claim 10, wherein the rate-controlling membrane comprises the pressure sensitive adhesive.

12. The system of claim 1, wherein the therapeutic agent comprises at least one of a tetracycline, a rifamycin, a macrolide, a penicillin, a cephalosporin, an aminoglycoside, a glycopeptide, a quinolone, fusidic acid, trimethoprim, metronidazole, mupirocin, a polene, an azole, a beta-lactam inhibitor, bacitracin, neomycin, tigecycline, daptomycin, or clindamycin.

* * * * *